US006653089B2

(12) United States Patent
Takayama et al.

(10) Patent No.: US 6,653,089 B2
(45) Date of Patent: Nov. 25, 2003

(54) DIFFERENTIAL TREATMENT OF SELECTED PARTS OF A SINGLE CELL WITH DIFFERENT FLUID COMPONENTS

(75) Inventors: Shuichi Takayama, Ann Arbor, MI (US); Emanuele Ostuni, Cambridge, MA (US); Philip LeDuc, Boston, MA (US); Keiji Naruse, Nagoya (JP); Donald E. Ingber, Boston, MA (US); George M. Whitesides, Newton, MA (US)

(73) Assignees: President and Fellows of Harvard College, Cambridge, MA (US); Children's Medical Center Corporation, Boston, MA (US)

( * ) Notice: Subject to any disclaimer, the term of this patent is extended or adjusted under 35 U.S.C. 154(b) by 0 days.

(21) Appl. No.: 09/954,978

(22) Filed: Sep. 18, 2001

(65) Prior Publication Data

US 2002/0146822 A1 Oct. 10, 2002

Related U.S. Application Data

(60) Provisional application No. 60/233,157, filed on Sep. 18, 2000.

(51) Int. Cl.[7] ............................................... G01N 33/53
(52) U.S. Cl. ........................ 435/7.72; 435/7.8; 435/29; 435/377; 435/378; 435/396; 435/397; 435/402; 435/287.1
(58) Field of Search ........................... 435/6, 7.72, 7.8, 435/29, 377, 378, 396, 397, 402, 287.1

(56) References Cited

U.S. PATENT DOCUMENTS

| 4,356,217 | A | 10/1982 | Wollam et al. |
| 4,411,218 | A | 10/1983 | Wollam et al. |
| 4,902,629 | A | 2/1990 | Meserol et al. |
| 5,131,907 | A | 7/1992 | Williams et al. |
| 5,222,808 | A | 6/1993 | Sugarman et al. |
| 5,300,779 | A | 4/1994 | Hillman et al. |
| 5,707,799 | A | 1/1998 | Hansmann et al. |
| 5,716,852 | A | 2/1998 | Yager et al. |
| 5,928,880 | A | 7/1999 | Wilding et al. |
| 5,955,029 | A | 9/1999 | Wilding et al. |
| 6,184,029 | B1 | 2/2001 | Wilding et al. |
| 6,355,198 | B1 | 3/2002 | Kim et al. |

FOREIGN PATENT DOCUMENTS

| WO | WO 96/29629 A2 | 9/1996 |
| WO | WO 97/33737 A1 | 9/1997 |
| WO | WO 97/45730 A1 | 12/1997 |
| WO | WO 01/89788 A2 | 11/2001 |
| WO | WO 02/22787 A2 | 3/2002 |

OTHER PUBLICATIONS

Takayama et al., Proc. Natl. Acad. Sci., vol. 96, May 1999, pp. 5545–5548.*
A. Ashkin et al., "Optical trapping and manipulation of single cells using infrared laser beams," Nature, vol. 330, pp. 769–771, Dec. 1987.
G. Blankenstein & U.D. Larsen, "Modular concept of a laboratory on a chip for chemical and biochemical analysis," Biosensors & Bioelectronics, vol. 13, No. 3–4, pp. 427–438, 1998.
F. Bradke & C.G. Dotti, "The role of local actin instability in axon formation," Science, vol. 283, pp. 1931–1934, Mar. 1999.
J.P. Brody et al., "Biotechnology at low reynolds numbers," Biophysical Journal, vol. 71, pp. 3430–3441, Dec. 1996.
D.T. Chiu et al., "Patterned deposition of cells and proteins onto surfaces by using three–dimensional microfluidic systems," Proc. Natl. Acd. Sci. USA, vol. 97, No. 6, pp. 2408–2413, Mar. 2000.
S.K.W. Dertinger et al., "Generation of gradients having complex shapes using microfluidic networks," Analytical Chemistry, vol. 73, No. 6, pp. 1240–1246, Mar. 2001.
D.C. Duffy et al., "Rapid prototyping of microfluidic switches in poly(dimethyl siloxane) and their actuation by electro–osmotic flow," J. Micromech. Microeng., vol. 9, pp. 211–217, 1999.
M. Jacoby, "Even flow builds microstructures," C&EN, p. 4, Jul. 1999.
N.L. Jeon et al., "Generation of solution and surface gradients using microfluidic systems," Langmuir, vol. 16, pp. 8311–8316, 2000.
A.E. Kamholz et al., "Quantitative analysis of molecular interation in a microfluidic channel: The T–sensor," Anal. Chem., vol. 71, pp. 5340–5347, 1999.
P.J.A. Kenis et al., "Microfabrication inside capillaries using multiphase laminar flow patterning," Science, vol. 285, pp. 83–85, Jul. 1999.
T.S.J. Lammerink et al. "Modular concept for fluid handling systems, A demonstrator Micro Analysis System," IEEE, pp. 389–394, 1996.

(List continued on next page.)

Primary Examiner—James Ketter
(74) Attorney, Agent, or Firm—Wolf, Greenfield & Sacks, P.C.

(57) ABSTRACT

The present invention is directed, in certain embodiments, to improved, small scale systems and methods able to selectively treat parts of a single cell, including, in certain embodiments, portions of a main body portion of a single cell, and able, in certain embodiments, to establish long-term gradients of active substances within subcellular regions of a single cell. The present invention provides, in some embodiments, techniques for selectively contacting a portion of the surface of a biological cell with a fluid or fluid component carrying a particular potential for a biophysical or biochemical interaction with the cell, and simultaneously contacting a different portion of the surface of the cell with another fluid or fluid component having a different potential for the biophysical or biochemical interaction with the cell.

68 Claims, 7 Drawing Sheets

OTHER PUBLICATIONS

K. Macounová et al., "Generation of natural pH gradients in microfluidic channels for use in isoelectric focusing," Anal. Chem., vol. 72, pp. 3745–3751, 2000.

H. Mensinger et al., "Microreactor with integrated static mixer and analysis system," Micro Total Analysis Systems, Proceedings of the µTAS '94 Workshop, Nov. 21–22, 1994, Kluwer Academic Publishers, pp. 237–243, 1995.

S. Takayama et al., "Patterning cells and their environments using multiple laminar fluid flows in capillary networks," Proc. Natl. Acad. Sci. USA, vol. 96, pp. 5545–5548, May 1999.

B.H. Weigl & P. Yager, "Microfluidic diffusion–based separation and detection," Science, vol. 283, pp. 346–347, Jan. 1999.

* cited by examiner

DIFFERENTIAL TREATMENT OF SELECTED PARTS OF A SINGLE CELL WITH DIFFERENT FLUID COMPONENTS

RELATED APPLICATIONS

This non-provisional application claims the benefit under Title 35, U.S.C. §119(e) of co-pending U.S. provisional application serial No. 60/233,157, filed Sep. 18, 2000, incorporated herein by reference.

GOVERNMENT SUPPORT STATEMENT

This application was sponsored by NIH Grant No. GM30367; NSF Grant No. ECS-9729405; ONR Grant No. N65236-07-1-5814; AFOSR/SPAWAR N66001-98-1-8915. The government has certain rights in the invention.

FIELD OF THE INVENTION

The present invention relates generally to systems and methods for selectively treating selected regions of an individual biological cell, and more particularly to systems and techniques utilizing laminar flow channel systems for such treatment.

BACKGROUND OF THE INVENTION

Complex behavior of cells, for example mitosis, growth, movement, metabolism, differentiation, apoptosis, etc. reflect integration of processes occurring in separate micro domains. Investigation of such behaviors require methods for delivering reagents to and/or into cells with subcellular resolution. Currently available techniques now used for micro manipulation of cells, for example micro injection, manipulation using mechanical or optical systems, etc., can, in some instances, provide subcellular resolution, but suffer from various limitations.

For example, micro manipulation techniques, such as the use of optical tweezers (Ashkin, A. and Dziedzic, J. M., "Internal cell manipulation using infrared laser traps," *Proc. Natl. Acad. Sci. USA*, vol. 86, 7914–7918 (1989), can provide limited subcellular spatial resolution, but such techniques are limited in their molecular specificity. Microinjection techniques can provide molecular specificity; however, they lack spatial control due to the rapid diffusion of small molecules within the cell. In addition, techniques such as microinjection also require physical disruption of the cell plasma membrane in order to provide reagents to the interior of the cell.

Microfluidic systems utilizing a multi-component laminar flow stream have been employed to create microfluidic sensor systems. Such microfluidic sensor systems are described, for example in Weigl, B. H. and Yager, P., "Microfluidic Diffusion-based Separation and Detection," *Science* 283, 346–347 (1999). Kennis et al., "Micro Fabrication Inside Capillaries Using Multi Phase Laminar Flow Patterning", *Science*, Vol. 285 (1999) describes the use of a laminar flow based microfluidic system for fabricating microstructures in capillaries. Takayama, et al., "Patterning Cells and Their Environment Using Multiple Laminar Fluid Flows and Capillary Networks," *Proc. Natl. Acad. of Sci. USA*, Vol. 96 (1999) describes using similar laminar flow based microfluidic networks to facilitate the spatial patterning of cells on a substrate and to provide a selected fluid environment to cells attached to a substrate.

Laminar flow occurs when two or more streams having a certain characteristic (low Reynolds number) are joined into a single, multi-component stream, also characterized by a low Reynolds number, such that the components are made to flow parallel to each other without turbulent mixing. The flow of liquids in small capillaries often is laminar. For a discussion of laminar flow and a definitions of the Reynolds number, the reader is referred to any of a large number of treatises and articles related to the art of fluid mechanics, for example, see Kovacs, G. T. A., "Micromachined Transducers Sourcebook," WCB/McGraw-Hill, Boston (1998); Brody, J. P., Yager, P., Goldstein, R. E. and Austin, R. H., "Biotechnology at Low Reynolds Numbers,: *Biophys. J*, 71, 3430–3441 (1996); Vogel, S., "Life in Moving Fluids," Princeton University, Princeton (1994); and Weigl, B. H. and Yager, P., "Microfluidic Diffusion-based Separation and Detection," *Science* 283, 346–347 (1999), each incorporated herein by reference.

Analytical chemical techniques have utilized laminar flow to control the positioning of fluid streams relative to each other. U.S. Pat. No. 5,716,852 (Yager et al.), describes a chemical sensor including a channel-cell system for detecting the presence and/or measuring the presence of analytes in a sample stream. The system includes a laminar flow channel with two inlets in fluid connection with the laminar flow channel for conducting an indicator stream and a sample stream into the laminar flow channel, respectively. The indicator stream includes an indicator substance to detect the presence of the analyte particles upon contact. The laminar flow channel has a depth sufficiently small to allow laminar flow of the streams and length sufficient to allow particles of the analyte to diffuse into the indicator stream to form a detection area.

U.S. Pat. No. 4,902,629 (Meserol et al.), discusses laminar flow in a description of apparatus for facilitating reaction between an analyte in a sample and a test reagent system. At least one of the sample and test reagent system is a liquid, and is placed in a reservoir, the other being placed in a capillary dimensioned for entry into the reservoir. Entry of the capillary into the reservoir draws, by capillary attraction, the liquid from the reservoir into the capillary to bring the analyte and test reagent system into contact to facilitate reaction.

A variety of references describe small-volume fluid flow for a variety of purposes. U.S. Pat. No. 5,222,808 (Sugarman et al.), describes a capillary mixing device to allow mixing to occur in capillary spaces while avoiding the design constraints imposed by close-fitting, full-volume mixing bars. Mixing is facilitated by exposing magnetic or magnetically inducible particles, within the chamber, to a moving magnetic field.

U.S. Pat. No. 5,300,779 (Hillman et al.), describes a capillary flow device including a chamber, a capillary, and a reagent involved in a system for providing a detectable signal. The device typically calls for the use of capillary force to draw a sample into an internal chamber. A detectable result occurs in relation to the presence of an analyte in the system.

International Patent Publication No. WO 97/33737, published Mar. 15, 1996 by Kim et al., describes modification of surfaces via fluid flow through small channels, including capillary fluid flow. A variety of chemical, biochemical, and physical reactions and depositions are described.

Typical prior art techniques employed for selectively treating single cells or supplying an active substance to the interior of a biological cell are unable to create long-term intracellular gradients, particularly of small molecules (e.g. those with molecular weights less than about 600 and having diffusion coefficients within the cell of more than about $10^{-6}$ cm$^2$/s). Microinjection studies and fluorescence recovery after photobleaching (FRAP) studies have shown that such small molecules will diffuse throughout the cytoplasm or myoplasm of a typical mammalian cell attached to a substrate (e.g., an attached mammalian cell having a maximum spread dimension of about 130 µm) within seconds the intracellular distribution of the molecules will reach 95% of an equilibrium distribution (i.e., there will be no region within the interior of the cell having a concentration of the molecule differing from another region of the cell by more than about 5%) within about 2 to about 5 minutes, even in the presence of some reversible binding of the molecule to immobilized cellular components, which binding tends to decrease the apparent diffusion coefficient (e.g. see Mastro, A. M., Babich, M. A., Taylor, W. D., and Keith, A. D., "Diffusion of small molecules in the cytoplasm of mammalian cells," *Proc. Natl. Acad. Sci. USA*, Vol. 81, 3414–3418 (1984); and Blatter, L. A. and Wier, W. G., "Intracellular diffusion, binding, and compartmentalization of the fluorescent calcium indicators indo-1 and fura-2," *Biophys. J,* Vol. 58, 1491–1499 (1990)). Thus, such methods are not well suited for creating intracellular gradients of such molecule having long-term duration.

Bradke and Dotti, "The Role of Local Actin Instability in Axon Formation," *Science*, Vol. 283, 1999, describe a micropipetting technique for selectively treating a region of an axon of a neuron with a cytoskeletal disrupting substance. The technique described utilizes selectively positioned micropipettes to direct a flow of liquid containing the cytoskeletal disrupting substance such that it impinges upon a portion of the axon extending away from the main body portion of the cell. By using this technique, the actin cytoskeleton in the region of the axon upon which the fluid impinges can be selectively depolymerized. The technique described, however, is only able to create a flowing fluid over a portion of the cell, with the rest of the cell submerged in quiescent fluid. Also, the micropipetted fluid will have a tendency to undergo convective mixing with the quiescent fluid surrounding the cell, making the technique potentially poorly suited for selectively treating parts of the main body portion of the cell.

While the above and other references describe useful techniques for chemical, biochemical, and physical modifications of surfaces, analytical detection, and the treatment of single cells with desired substances, a need exists for improved, small scale systems and methods able to selectively treat parts of a single cell, including portions of a main body portion of a single cell, and able to establish long-term gradients of active substances within subcellular regions of a single cell.

SUMMARY OF THE INVENTION

The present invention is directed, in certain embodiments, to improved, small scale systems and methods able to selectively treat parts of a single cell, including, in certain embodiments, portions of a main body portion of a single cell, and able, in certain embodiments, to establish long-term gradients of active substances within subcellular regions of a single cell. The present invention provides, in some embodiments, techniques for selectively contacting a portion of the surface of a biological cell with a fluid or fluid component carrying a particular potential for a biophysical or biochemical interaction with the cell, and simultaneously contacting a different portion of the surface of the cell with another fluid or fluid component having a different potential for the biophysical or biochemical interaction with the cell.

In one aspect, a method is disclosed, the method comprising establishing a flowing stream of a fluid against a surface of a cell, the stream including at least first and second components in contact with first and second portions of the cell, respectively. The first component of the stream includes therein, at a first concentration, a substance able to bind to the surface of the cell, permeate across the cell plasma membrane into the interior of the cell, or both. The second component of the stream has a second concentration of the substance therein. The method further comprises binding the substance to the surface of the first portion of the cell, permeating the substance across the cell plasma membrane of the first portion of the cell, or both, to an extent different than that at the second portion of the cell.

In another embodiment, a method is disclosed, the method comprising selectively providing to a first portion of the exterior of a cell a first flowing fluid containing a substance able to effect a biochemical or biophysical interaction within the cell. The method further comprises selectively providing to a second portion of the exterior of the cell a second flowing fluid removing from the second portion of the exterior of the cell said substance, thereby establishing within the cell a gradient of an active substance.

In another embodiment, a method is disclosed, the method comprising selectively exposing a first portion of the exterior of a cell to a first fluid containing a substance able to effect a biochemical or biophysical interaction within the cell, the first portion of the exterior of the cell comprising a portion of a main body of the cell, and selectively exposing a second portion of the exterior of the cell to a second fluid removing from the second portion of the exterior of the cell said substance, thereby establishing within the cell a gradient of an active substance. The gradient being characterized by the existence of a first region within the cell, proximate to at least a portion of the first portion of the exterior of the cell, having a first concentration of the active substance and the existence of a second region within the cell, proximate to at least a portion of the second portion of the exterior of the cell, having a second concentration of the active substance, the first concentration of the active substance differing from the second concentration of the active substance by at least about 5% at a time exceeding about 5 min after the cell was first exposed to the first and second fluids.

In yet another embodiment, a method is disclosed, the method comprising establishing within a cell a gradient of a freely diffusable active substance, characterized by the existence of a first region within the cell having a first concentration of the active substance and the existence of a second region within the cell having a second concentration of the active substance, the first concentration of the active substance differing from the second concentration of the active substance by at least about 5% at a time exceeding about 5 min after the commencement of the establishment of the gradient.

In yet another embodiment, a method is disclosed, the method comprising creating a first region within a cell of a selected cell type, the first region containing freely diffusable active substance, the first region comprising a portion of a main body of the cell. The method further comprises creating a second region within the cell essentially free of freely diffusable active substance. The method also involves detecting, for each of the first and second regions, at least one parameter indicative of a response of the cell to the active substance determinative of the efficacy of a treatment with the active substance on the cell type.

In another embodiment, a method is disclosed, the method comprising allowing a substance to bind to a first region of the exterior of a cell membrane of a selected cell type and creating a second region of the exterior of the cell membrane that is essentially free of the bound substance. The method also involves detecting, for each of the first and second regions, at least one parameter indicative of a response of the cell to the bound substance determinative of the efficacy of a treatment with the substance on the cell type.

In yet another embodiment, a method is disclosed, the method comprising selectively providing to a first portion of the plasma membrane of a cell a first flowing fluid containing therein a substance, which is able to permeate across the plasma membrane, at a concentration exceeding or equal to a maximum concentration of the substance within the cell, and selectively providing to a second portion of the plasma membrane of the cell a second flowing fluid containing therein a concentration of the substance, which is able to permeate across the plasma membrane, less than or equal to a minimum concentration of the substance within the cell.

In another embodiment, a method is disclosed, the method comprising establishing a flowing stream of a fluid against a surface of a cell, the stream including at least first, second and third components in contact with first, second, and third portions of the cell, respectively, the second component of the stream being interposed between the first component of the stream and the third component of the stream. The first component of the stream and the third component of the stream each carry a different potential for a biophysical or biochemical interaction with the cell than the second component of the stream. The method further involves carrying out the biophysical or biochemical interaction at the first and third portions of the cell to an extent different than at the second portion of the cell.

In yet another embodiment, a method is disclosed, the method comprising establishing a flowing stream of a fluid, the stream including at least first and second components adjacent to each other and defining therebetween a boundary. The method further includes carrying out a biophysical or biochemical interaction at a first portion of a cell proximate the boundary selectively, to an extent different than at a second portion of the cell.

In another aspect, an article is disclosed. The article comprises a substrate having at least one cell positioned on a surface of the substrate and a flowing fluid stream in contact with the surface. The stream includes at least first and second components in contact with first and second portions of the cell, respectively. The first component of the stream included therein at a first, essentially uniform concentration a substance able to bind to an exterior surface of the cell, permeate across the cell membrane into the interior of the cell, or both. The second component of the stream has a second, essentially uniform concentration of the substance therein.

Other advantages, novel features, and objects of the invention will become apparent from the following detailed description of the invention when considered in conjunction with the accompanying drawings, which are schematic and which are not intended to be drawn to scale. In the figures, each identical or nearly identical component that is illustrated in various figures is represented by a single numeral. For purposes of clarity, not every component is labeled in every figure, nor is every component of each embodiment of the invention shown where illustration is not necessary to allow those of ordinary skill in the art to understand the invention.

DETAILED DESCRIPTION

Figure 1A:
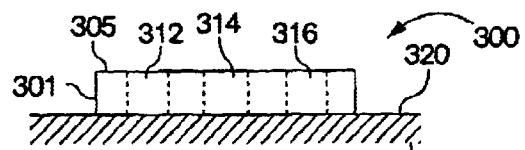
FIG. 1A is a schematic, side view of one embodiment of a microfluidic system.
Figure 1B:
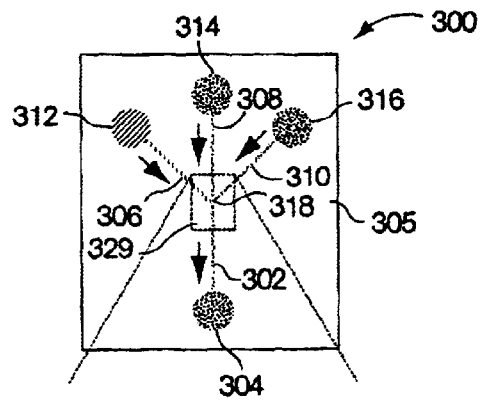
FIG. 1B is a schematic, en face view of the microfluidic system of FIG. 1A.

The present invention is directed to techniques for selectively contacting a portion of the surface of a biological cell with a fluid or fluid component carrying a particular potential for a biophysical or biochemical interaction with the cell, and simultaneously contacting a different portion of the surface of the cell with another fluid or fluid component having a different potential for the biophysical or biochemical interaction with the cell. In addition to contacting a single cell with two fluid components, as described above, it should be understood, and is described in more detail below, that the cell may be contacted with a plurality of such fluid components, for example, three, four, five, or more of such fluid components.

Biophysical or biochemical interactions that occur at or within a region or portion of a cell interior or surface of a cell to an extent different from another region or portion can occur at at least a 5% difference, 10% difference, 20%, 30%, 40% difference, or other percentage difference, up to a 100% difference.

In preferred embodiments, at least one of the fluids or fluid components that makes contact with a portion of the cell, as described above, is a flowing stream of fluid, and in the most preferred embodiments, each of the fluids or fluid components in contact with the cell are configured as flowing streams. In a particularly preferred embodiment, the cell is selectively exposed to multiple components of a fluid by establishing a flowing stream of a fluid against the surface of the cell, where the flowing stream includes at least a first and second component, and in some embodiments more than a first and second component, in contact with first and second portions of the cell, respectively, A "fluid" as used herein refers to essentially any fluent material in a liquid, gas, and/or supercritical state. Typically, for the embodiments wherein the fluid is in contact with a portion of a biological cell, the fluid will comprise an aqueous liquid, which is physiologically compatible with the cell, for example, a physiological media or buffer. A "stream" of a fluid, as used herein, refers to a flowing fluid having a continuous, non-physically separated, wetted cross-section (i.e., configured as a single continuous stream as opposed to two or more separated streams that are not adjacent and in contact with each other). In particularly preferred embodiments, described in more detail below in the context of FIGS. 1–3, the flowing stream of fluid is contained within a conduit of a microfluidic flow system or network having at least one surface thereof on which an at least one cell, and typically a plurality of cells, is attached (e.g. see FIGS. 1C and 3B).

A "component" of a fluid or flowing fluid stream, or, equivalently, a "fluid stream" when used in the contact of at least two such streams flowing parallel, adjacent, and in contact to each other, or, similarly, a "first fluid", "second fluid", etc., when used in the context of describing a particular region of a physically continuous body of fluid in contact with a portion of the cell surface refers to a region of the fluid or fluid stream that is characterized by at least one bulk property which differs from, and is in non-equilibrium with respect to, a similar bulk property of another component of the fluid in contact with the cell surface. A "bulk property" is determined as the average value of the particular property over the cross-section, taken perpendicular to the direction of flow for flowing streams, of the component. The property can be any property which, as described above, is able to carry a potential for a biophysical or biochemical interaction with the cell. The property can be a chemical and/or physical property such as, for example, the presence or absence of a particular solvent and/or dissolved solute/substance; a concentration of solute/substance; temperature; velocity; etc.

"Adjacent" components, fluids, or streams are those positioned next to and in contact with each other. Such adjacent components are typically characterized by a region of discontinuity in the spatial distribution of at least one property, the region of discontinuity defining an "interface" or "boundary" between the components. For one example, a fluid stream can have a first component with a first bulk concentration of a substance, which is essentially uniform throughout the cross-section of the first component, and an adjacent, second component with a second bulk concentration of the substance, which is essentially evenly or uniformly distributed within the cross-section of the second component, with an interface/boundary between the components characterized by a gradient of the substance caused by diffusional mixing between the adjacent components.

In general, and as discussed in more detail below, in preferred embodiments, the diffusional boundary or interface between components of the fluid streams in contact with the cell surface are minimized in cross-sectional dimension, so as to provide as sharp a transition as practical between the bulk properties of the components of the fluid stream in contact with the cell surface.

In particularly preferred embodiments, components of a flowing stream of fluid are arranged, relative to each other, via laminar flow convergence. Techniques for facilitating laminar flow are known. Some known techniques involve creating a side-by-side parallel, contacting multiple flowing streams/components of a flowing stream, that are free of turbulent mixing, but are eventually allowed to mix, at the interface between the components, by diffusion to allow analytical detection. Some preferred embodiments of the present invention utilize laminar flow to create multi-component fluid streams that flow over selected portions of a single cell's surface, and are free of turbulent mixing across such portions. In such laminar flow streams, mixing occurs only via diffusion at the interfaces of components of the fluid stream.

Techniques of the present invention can be carried out by flowing fluid streams within channels of a variety of shapes and dimensions, which are sized and configured to prevent turbulent mixing of the streams and maintain laminar flow therein. A wide variety of such techniques for creating laminar flow of fluid streams are known, including the use of microfluidic systems for creating multi-component laminar flow streams such as those useful in the context of the present invention. Accordingly, such systems will not be discussed exhaustively in detail herein. Such systems, and techniques for establishing and maintaining multi-laminar flow streams with such systems are described in detail, for example, in Kovacs, G. T. A., et al., 1998; Brody, J. P. et al., 1996; Vogel, S., 1994; and Weigl, B. H., et al. 1999 (each previously incorporated herein by reference), and Kamholz, A. E., Weigl, B. H., Finlayson, B. A., and Yager, P., "Quantitative Analysis of Molecular Interaction in a Microfluidic Channel: The T-Sensor," *Anal. Chem.* vol. 71 (1999); and Takayama, S., McDonald, J. C., Ostuni, E., Liang, M. N., Kenis, P. J. A., Ismagilov, R. F., and Whitesides, G. M., "Patterning cells and their environments using multiple laminar fluid flows in capillary networks," *Proc. Natl. Acad. Sci. USA,* vol. 96 (1999), each incorporated herein by reference. Those of ordinary skill in the art, upon reading the reading the present disclosure, will be able to readily construct systems for providing multi-component laminar flow streams to carry out techniques of the present invention, without undo experimentation.

In certain preferred embodiments, the bulk property of the fluid stream components creating the potential for biophysical or biochemical interaction with a cell is a concentration of a substance within the fluid in contact with the surface or the cell, which substance is able to bring about a biophysical and/or biochemical interaction within the cell and/or upon the surface of the cell. For example, in one embodiment the substance binds to the surface of the cell. In such embodiments, the substance can be, for example, a ligand, hapten, protein, glycoprotein, lipoprotein, carbohydrate, etc., which is able to selectively bind to a particular cell surface receptor. Such substances, which can selectively bind to components of the surface of the cell can, in some embodiments, subsequently be endocytosed or otherwise transported into the interior of the cell, or can effect, in other embodiments, the physiology/function of the cell (e.g. establish an intracellular gradient of an active substance) via transmembrane signaling, receptor aggregation, or other known phenomena.

In another embodiment, the substance is selected so that it is able to permeate across the cell plasma membrane into the interior of the cell, either by passive transport through the plasma membrane and/or active transport through the cell plasma membrane. As described above, substances which are able to permeate across the cell plasma membrane can be useful, within the context of an inventive method for creating long-term intracellular gradients of such substances within the interior of the cell. In yet other embodiments, the substance can be chosen to be able to degrade and/or depolymerize a portion of the cell surface and/or a protein or other molecule attached to the cell surface, for example a protein such as fibronectin, through a cell is attached to a substrate within the system. While particular exemplary applications of the use of the present inventive techniques for selectively contacting portions of a cell with components of a fluid stream are described in more detail below, those of ordinary skill in the art will readily appreciate, in view of the above discussion and subsequent disclosure, that the techniques provided according to the invention have an extremely wide applicability for enabling the study, assay, detection, etc. of an extremely wide variety of cell parameters, functions, behavior, responses, etc. to an extremely wide variety of bulk properties and substances able to affect a biophysical and/or biochemical interaction with a cell. Each such application and use of the present invention is deemed to be within the scope of the present invention as described in the claims below.

In preferred embodiments of the techniques provided according to the invention, wherein multiple components of a flowing fluid stream differ from each other with respect to the concentration of a substance within at least one of the components, the concentration of the substance is essentially uniform in at least a portion of at least one of the components in contact with the cell, or preferably is essentially uniform in at least a portion of each of the components in contact with the cell, and most preferably is essentially uniform in essentially the entirety of each component in contact with portions of the cell. "Essentially uniform" as used herein in the context of the concentration of a substance in a component refers to the concentration of the substance at issue being essentially uniform across the cross-section of the component of the stream, which concentration differs from that of an adjacent component of the stream.

For embodiments where a flowing stream of fluid has multiple flowing components characterized by laminar flow, which components are in contact with different portions of a single cell, because of the stability, lack of turbulent mixing, and ability to create a sharp interface between the components, as discussed in more detail below, the portions of the cell contacted by different components of the flowing stream can be portions of the main body portion of the cell. The "main body portion of the cell" as used herein refers to the region of the cell excluding small diameter protuberances, extensions, processes, etc. The main body portion of the cell, as used herein, has a minimum cross-sectional dimension, measured along at least one given direction, that is at least 10% of the maximum cross-sectional dimension of the cell, as measured along the same given direction. Thus, the techniques provided according to the invention can enable various portions of the main body portion of a cell to be partitioned and selectively contacted with various components of a flowing stream having a different potential for effecting a biophysical and/or biochemical interaction with the cell. Such subcellular resolution and control of the delivery of fluids to selected regions of cells is not typically available with prior art techniques for treating single cells.

Another aspect of the inventive techniques involves the ability to establish within a cell a gradient of an active substance. An "active substance" as used herein in the present context refers to a substance that is present within the interior of the cell and is able to effect a biophysical and/or biochemical change in the cell. Certain embodiments of the inventive techniques described herein are able to create long-term gradients of an active substance within the cell. A "long-term gradient" of an active substance within a cell as used herein refers to a gradient that is characterized by the existence of a first spatial region within the cell having a first concentration of the active substance and the existence of a second spatial region within the cell having a second concentration of the active substance, where the first concentration of the active substance differs from the second concentration of the active substance by at least about 5%, more preferably 10%, more preferably 20%, more preferably 30%, more preferably 40%, more preferably 50%, more preferably 60%, more preferably 70%, more preferably 80% more preferably 90%, most preferably 100%, at a time that exceeds about 5 minutes, more preferably about 10 minutes, more preferably about 20 minutes, most preferably about 30 minutes after the establishment of the gradient within the cell. In some especially preferred embodiments of the inventive technique, a gradient is established within the cell that is an essential steady state gradient, in other words where the above-mentioned differences in concentration between a first region of the interior of the cell and a second region of the interior of the cell are maintained indefinitely.

As discussed in more detail below, certain embodiments of the inventive technique are able to establish such long-term or steady state gradients of an active substance within the cell even for active substances that are freely diffusable within the cell or for active substances where some of the molecules thereof are freely diffusable within the cell, while others are reversibly or irreversibly bound to immobile structures (within the time scale of the experiment) within the cell. An active substance that is "freely diffusable" or a "freely diffusable" portion of an active substance (i.e. the unbound molecules of an active substance having some molecules that become bound and others that remain unbound) within the cell as used herein refers to the molecules of such substance being not bound to, either reversibly or irreversibly, any internal components of the cell so that they become immobilized within the cell; in other words the molecules of such substance are free to diffuse throughout the cytoplasm of the cell.

The active substance forming the gradient within the cell can, in some embodiments, be a substance that is non-permeable with respect to the plasma membrane of the cell. In such embodiments, the gradient of the active substance can be established, for example, by exposure of a portion of the external surface of the plasma membrane of the cell to a substance or other condition which, through transmembrane signaling, or other mechanism, is able to establish the gradient of the intracellular active substance.

In more typical embodiments, the active substance forming the gradient within the cell is a substance that is able to permeate across the cell's plasma membrane by either or both of passive diffusion and active transport. In preferred embodiments, the intracellular gradient of the active substance is established within the cell by selectively exposing a first portion of the exterior of the cell to a fluid, or component of a fluid stream, that contains a substance able to affect the concentration or distribution of the active substance within the interior of the cell and, simultaneously, exposing a second portion of the exterior of the cell to another fluid, or component of a fluid stream, for removing from the second portion of the exterior of the cell the substance able to affect the concentration or distribution of the active substance within the interior of the cell.

In certain preferred embodiments, the active substance forming a gradient within the cell is permeable through the plasma membrane of the cell and is selectively supplied to a first portion of the exterior surface of the plasma membrane of the cell while being simultaneously removed from a second portion of the exterior surface of the plasma membrane of the cell, thereby establishing the gradient of the active substance within the cell. In such embodiments, where, for example, the exterior of the cell is in contact with two components of a multi-component flowing stream, a first component of the fluid stream containing the substance and supplying it to the plasma membrane of the cell should contain the substance at a concentration that exceeds or is equal to the maximum concentration of the active substance within the cell, and a second component of the flowing stream removing the substance from the surface of the plasma membrane should contain the substance at a concentration that is less than or equal to the minimum concentration of the substance within the cell (e.g. be essentially free of the substance).

As is described in more detail below with reference to FIG. 2, for intracellular gradients that are established by substances that are supplied to the exterior of the cell membrane and permeate through the cell, thereby forming the intracellular gradient, long-term and steady state gradients are most effectively established when utilizing substances that are comprised of relatively small molecules (e.g., having molecular weights less than about 600) and which have relatively high ratio of their permeability constant through the plasma membrane to their diffusion constant in the cytoplasm of the cell (see for example FIGS. 2A–C and associated discussion).

In general, when an intracellular gradient of an active substance is established within a cell by selectively exposing a first portion of the exterior of a cell to a first fluid or first component of a fluid stream supplying a substance to the first portion of the exterior of the cell and selectively exposing a second portion of the exterior cell to a second fluid or second component of a fluid stream removing the substance from the second portion of the exterior of the cell, the gradient of the active substance within the cell will be established such that there is a first region within the cell, proximate to at least a portion of the first portion of the exterior of the cell, which first region will have a first concentration of the active substance, and the existence of a second region within the cell proximate to at least a portion of the second portion of the exterior of the cell, which second region will have a second concentration of the active substance less than the first concentration. Also, in general, the greater the difference between the concentration of the substance in the first fluid or first fluid component supplying the substance of the cell surface and the concentration of the same substance in the second fluid or second fluid component removing the substance from the cell surface, the greater will be the differences in concentration within the cell of the active substance between the first region of the cell and the second region of the cell defining the intracellular gradient. In particularly preferred embodiments, the second fluid or second component of a fluid stream removing the substance from the surface of the cell is essentially free of the substance prior to contact with the external surface of the cell. By careful selection of operating parameters according to the teachings described herein, and routine experimentation, intracellular gradients of active substances can be established within cells such that certain, selected regions of the interior of the cell contain the active substance, while other regions of the interior of the cell are essentially free of the active substance, even for active substances that are freely diffusable within the cell and freely permeable across the plasma membrane of the cell.

As described in more detail below, the ability to establish long-term and steady state gradients of active substances within a cell, can enable a wide variety of tests, determinations and assays based on measurements or observations of a single cell that were previously unobtainable using typical prior art techniques and systems. For example, the ability to establish intracellular gradients by selectively supplying small, membrane-permeable molecules to selected portions of an exterior cell surface and removing the same from other portions of the same cell surface can enable a high degree of localization of such small molecules to subcellular microdomains within the cell, thus facilitating studies directed to determining the effect of such molecules on the subcellular microdomains, and/or to the spatial distribution and redistribution of subcellular microdomains with respect to various cell treatments. For example, as described in more detail below in the context of FIG. 2 and in the examples, the inventive techniques for establishing intracellular gradients can be utilized for detecting a parameter (e.g., fluorescence intensity) indicative of a spatial distribution of an active substance within the cell, a measure of the relative permeability of the plasma membrane of the cell to the active substance and/or a measure of the relative thickness of the cell (e.g., for a cell attached and spread to a substrate) at a selected location within the cell.

In addition to the above-mentioned applications wherein the establishment of an intracellular gradient using the inventive techniques can be utilized for determining and/or studying physical properties of the cell such as thickness and membrane permeability, the ability to selectively deliver substances to portions of a cell while removing the substances from other portions of the cell, thereby establishing a long-term or steady state gradient of the active substance within the cell can enable assays which utilize a single cell as both a test and control. Such assays can be useful for studying intracellular trafficking and distribution of subcellular microdomains as well as to study biophysical or biochemical effects on a cell, or the efficacy of a treatment of a cell type with, various drugs, such as growth factors or cancer drugs.

For such applications, it is preferable to establish an intracellular gradient of the active substance characterized by the existence of one region of the interior of the cell containing the active substance and a second region of the interior of the cell essentially free of the active substance, preferably having a volume similar to, or a substantial fraction of, the region containing the active substance. In this way, the region of the interior of the cell containing the active substance acts as a "test region" and the region that is essentially free of the active substance acts as a built-in "control region" of the cell.

In one exemplary embodiment, the active substance is a drug or other substance able to disrupt or stabilize a cytoskeleton of the region of the interior of the cell containing the active substance. In some especially preferred embodiments, the cytoskeletal disrupting or stabilizing substance is an anti-cancer drug (e.g., Taxol). In another such embodiment, or as part of the above-mentioned embodiment involving cytoskeletal disrupting or stabilizing substances, a portion of the interior of the cell can be selectively treated with a substance able to localize within a subcellular organelle of the cell. For example, a substance can be chosen that is able to localize in a subcellular organelle of the cell which can be a fluorescent dye or label able to bind to the particular subcellular organelle and to enable the location and distribution of the organelles to be visually monitored or detected. A variety of such dyes and other substances able to localize in selected subcellular organelles are readily available and well known to those of ordinary skill in the art, a few of which are discussed below in the examples section.

By selectively treating one region of a cell with a membrane-permeable dye able to localize in a particular subcellular organelle, such as mitochondria or golgi, as described above, the trafficking and distribution of the labeled subcellular organelle, in response to a particular treatment or stimulus of the cell, can be monitored. In one embodiment the treatment or stimulus affecting the distribution or trafficking of the labeled subcellular organelles can be a selective stabilization or disassociation of the cytoskeleton in a particular region of the cell, as described above. Such a combined assay can potentially yield important information regarding the influence of the integrity of the cytoskeleton on the trafficking and intracellular motility of various subcellular organelles.

In addition to the above-described applications of the inventive methods for creating an intracellular gradient, a wide variety of other determinations and assays based on selective treatment of a portion of single cell can be enabled by the inventive technique of contacting selected portions of the exterior of the cell with different fluids or components of a fluid stream. Such applications include, but are not limited to, for example, determining the effect on a single cell of the binding of a substance having affinity for a particular cell surface receptor to receptors on only a selected portion of the cell membrane; investigating the migration and destination of drugs or other substances which bind to cell surface receptors and are subsequently endocytosed into the cell (e.g. low density lipoprotein) by selectively supplying such substances to only a portion of the exterior surface of the cell; and studying the effect of selective treatment of a portion the exterior of the cell with substances, such as drugs, which are able to affect calcium influx/efflux through cellular ion channels and/or are able to create or affect the establishment of intracellular calcium ion gradients; etc. In general, the inventive techniques can enable a single cell to be utilized as both a test and control for determining the effect, efficacy, etc of a given treatment with a membrane-permeable active substance on a particular cell type by, for example, detecting for each of a first treated and second untreated regions of a single cell at least one parameter indicative of a response of the cell to the active substance determinative of the efficacy of the treatment with the active substance on the cell type. Alternatively, the inventive techniques can enable a single cell to be utilized as both a test and control for determining the effect, efficacy, etc of a given treatment with a substance that binds to the exterior of a particular cell type by, for example, detecting for each of a first, treated and second, untreated regions of a single cell at least one parameter indicative of a response of the cell to the bound substance determinative of the efficacy of the treatment with the substance on the cell type.

The inventive techniques can enable various measurements and observations of cell behavior, such as the trafficking and transport of intracellular substances and subcellular organelles, not previously obtainable with typical prior art techniques. The inventive techniques can also enable various analytical tests and assays for evaluating treatment efficacy on cells of various substances, wherein by a single cell acting as both a test and a control, many statistical uncertainties inherent in studying the effects of such treatments on individual, whole cells within a population of a given cell type can be eliminated.

The inventive techniques and articles described herein are readily adaptable for use in automated systems for performing the above-described assays, tests, determinations, measurements, observations, etc. as well as many others, in an automated and fully controlled fashion. Described below, in the context of the figures and examples, is one specific embodiment of a microfluidic apparatus and system suitable for performing the inventive techniques described herein.

One embodiment of a microchannel system 300, constructed to enable a single cell to be contacted by more than one component of a flowing fluid stream, is illustrated schematically in FIGS. 1A–C and FIGS. 3A–B. A "microchannel system," or "microchannel device," or "microfluidic network," or "microfluidic system," or "microfluidic device" as used herein refers to an article, device, or system including at least one conduit or capillary therein capable of containing a flowing fluid, where the conduit or capillary has a maximum cross-sectional dimension, in a direction perpendicular to the direction of fluid flow in the capillary or conduit, not exceeding about 1 millimeter. It will be understood by those of ordinary skill in the art that a wide variety of techniques, substrates, and materials can be used for fabricating microfluidic networks or flow devices useful for performing the techniques disclosed herein. Such devices can be constructed, for example, of micro-fine glass capillaries, micro-machined and/or photolithographically machined silicon or other substrates, or a variety of other known methods capable of forming conduits, capillaries, or channels within the above-mentioned size range. The use of each of such devices is deemed to be within the scope of the present invention.

As previously discussed, preferred embodiments of microfluidic network system 300 are designed and constructed to enable the creation and maintenance of a laminarly flowing multi-component fluid stream in at least one channel of the network system. Laminar flow is characterized as flow for which the dimensionless Reynolds number, which is proportional to the density of the flowing fluid, the characteristic fluid speed, and the characteristic cross-sectional dimension of the channel in which the fluid flows and which is inversely proportional to the viscosity of the fluid, is less than about 2000. The equations and techniques for selecting parameters for fabricating microfluidic and other fluidic networks to enable such desired laminar flow are well known to those of ordinary skill in the art and are described, for example, in Brody, J. P., et al., 1996, and Kovacs, G. T. A., et al., 1998, both previously incorporated herein by reference; and in many standard fluid mechanics texts, for example, Bird R. B., Stewart W. E., and Lightfoot E. N., "Transport Phenomena," John Wiley & Sons, New York (1960) incorporated herein by reference.

The microfluidic network system illustrated in FIGS. 1A–C and 3A–B comprises an elastomeric micromolded slab or membrane 301, in the illustrated embodiment, constructed of poly(dimethylsiloxane) (PDMS), having a main flow channel 302, in which the multi-component laminar flow stream is formed, and three inlet channels 306, 308, and 310 feeding main flow channel 302 and converging at junction 318. The channels are in the form of rectangular troths comprising negative relief features in bottom surface 303 of slab 301. Inlet channels 306, 308, and 310 are in fluid communication with, and are fed by, inlet wells 312, 314, and 316, respectively which wells traverse the thickness of slab 301 and are open for filling at upper surface 305 of PDMS slab 301. The channels and wells are made fluid tight by contacting lower surface 303 of slab 301 with a substrate 320, such as a glass microscope slide, petri dish, cover glass, etc., thus forming a reversible, conformal seal. As a result, the substrate 320 forms the bottom surface of each of the microfluidic channels of the network. In other embodiments, slab 301 may be irreversibly and permanently sealed to substrate 320, if desired or the channels may be completely formed within the body of slab 301 such that conformal sealing to a substrate is not necessary to provide a completely enclosed flow channel.

Suitable micro replica-molding techniques for forming microfluidic network 300 are known in the prior art, and the reader is referred to Takayama, S., et al., 1999, previously incorporated herein by reference; and Duffy, D. C., McDonald, J. C., Schueller, J. A., and Whitesides, G. M., "Rapid Prototyping of Microfluidic Systems in Poly (dimethylsiloxane)," *Anal. Chem.*, Vol. 70, 4974–4984 (1998); and International Publication No. WO 97/33737 (Kim., E., et al., 1997), both incorporated herein by reference, for details of the fabrication procedure.

Microfluidic network 300 has a single main flow channel 302, in which multi-component laminar flow is established, and three inlet channels 306, 308, and 310 feeding the main flow channels and converging together at junction 318 in a fashion which forms a bisected "Y" shape. Each of the channels, in the illustrated embodiment, has a channel width, measured in a direction perpendicular to the fluid flow stream within the channel, of about 300 micrometers, and a channel depth of about 50 micrometers. Each of the inlet and outlet wells is sized to contain about 100 microliters of fluid and has a depth, providing a static pressure head for creating a driving force for fluid flow, equal to the thickness of slab 301, which, in the illustrated embodiment, is about 5 millimeters.

Microfluidic network system 300 has the capability of forming a fluid stream in main flow channel 302 that includes anywhere from one to three distinct, parallel flowing components. For example, by supplying three fluids, differing from each other in at least one bulk property (or at least differing from each fluid in adjacent wells), one fluid to each of the inlet wells, a flow stream with three components 330, 332, and 334, shown most clearly in FIGS. 1C and 1D, can be established in channel 302.

Figure 1C:
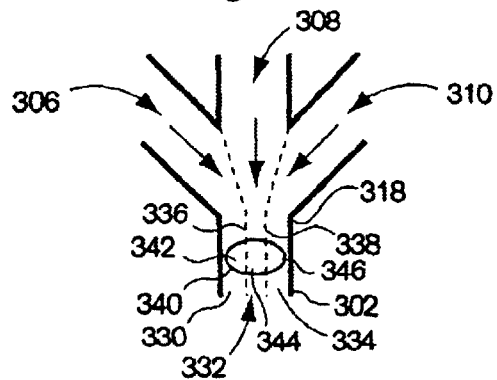
FIG. 1C is an enlarged view of a portion of the microfluidic system of FIG. 1B.
Figure 1D:
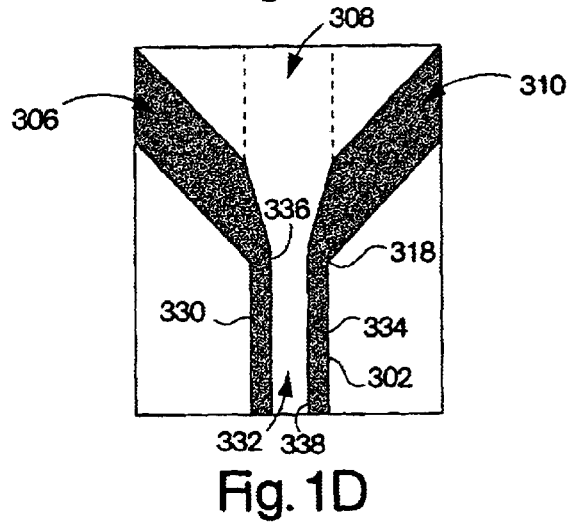
FIG. 1D is a photocopy of a fluorescence photomicrograph of a three-component fluid flow established a microfluidic system as shown in FIG. 1B.

FIG. 1D illustrates the results of creating such a three-component fluid stream in main channel 302. Shown in the figure is a photograph of area 329 of the microfluidic network after the establishment of a three-component flow in main channel 302. Component 330 comprises a fluid having therein a fluorescing substance as does component 334. Component 332, which forms the central component of the three component flow, comprises a fluid lacking the fluorescing substance of components 330 and 332, and thus appearing dark in the figure. It should be understood, that the illustrated embodiment having three inlet streams for forming a one- to three-component flow is merely exemplary and fewer or greater numbers of inlets may be configured to converge and feed a main channel to produce multi-component streams having anywhere from two components to a large number of components, for example, greater than ten components.

To establish the multi-component fluid stream in microfluidic network system 300, inlet wells 312, 314, and 316 are initially filled, for example completely filled to top surface 305 of slab 301, while outlet well 304 is maintained free of fluid, for example, by aspiration, blotting, etc. For the system illustrated, with inlet wells, 312, 314, and 316 completely filled with fluids having a similar density and viscosity and outlet well 304 maintained essentially free of fluid, the driving force provided by the difference in fluid height within the inlet wells as compared to the outlet well is sufficient to create a maximum bulk fluid velocity in main flow channel 302 of about 0.6 cm/s. The Reynolds number at such flow rate, for aqueous fluids, is very small (less than one), and, therefore, fluid stream components 330, 332, and 334 in main flow channel 302, flow next to each other without mixing, other than by diffusion, and without turbulence. Also, since microfluidic network system 300 is configured such that the resistance to fluid flow in each of the inlet channels feeding main channel 302 is about the same, the volumetric flow rate of each of components 330, 332, and 334 will be similar and each of the components will have a similar cross-sectional dimension, as measured in the direction perpendicular to the flow stream in the main channel (e.g. see FIGS. 1C and 1D).

In general, the width of each component of the fluid stream in the main channel will be directly proportional to the volumetric flow rate of each of the component streams, which, in turn, is proportional to the relative driving forces and resistances to flow of each of the feed channels feeding the main fluid flow channel containing the multi-component flow stream. Accordingly, the relative widths of the components of the flow stream in the main channel and the particular positions of the interfaces separating the flow streams can be controlled and predicted by controlling the volumetric flow rate of the streams feeding the main channel.

The volumetric flow rates of the individual inlet streams can be readily controlled, in the illustrated embodiment, by changing the relative height of the liquid column contained in one or more inlet wells with respect to other inlet wells of the system. In other embodiments, the volumetric flow rates of the individual feed streams can be adjusted by changing the geometry or channel size of one or more of the inlet channels to create a greater or lesser resistance to flow as compared to that provided by other inlet streams (for example, see "Pipe Friction Manual," 3rd. ed., Hydraulic Institute, New York (1961) and "Fluid Mechanics for Engineering Technology," 3rd. ed., Prentice Hall, Englewood, N.J. (1989), both incorporated herein by reference).

In another embodiment, the volumetric flow rate of each of the inlet streams could be adjusted and controlled by feeding each of the inlet streams directly with a pump, for example a syringe or peristaltic pump capable of pumping fluids at variable, small, volumetric flow rates. In general, those of ordinary skill in the fluid mechanical arts will readily envision a variety of ways of adjusting and controlling the relative flow rates of streams feeding a main channel of a microfluidic network for performing the inventive techniques, such that the components of the fluid stream in the main flow channel have desired dimensions with interfaces therebetween positioned at desirable, and reproducibly obtainable, positions within the main flow channel.

Figure 3A:
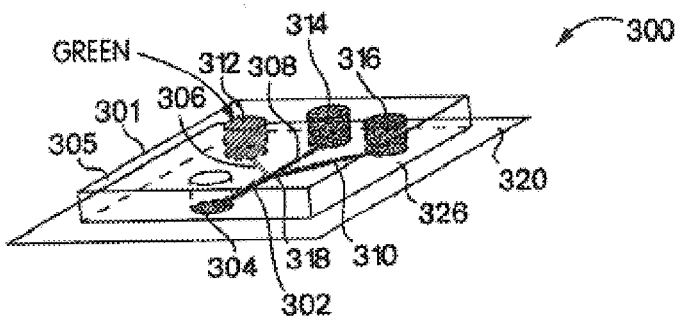
FIG. 3A is a schematic, perspective view of the microfluidic network of FIG. 1B as configured to create a two-component fluid stream.
Figure 3B:
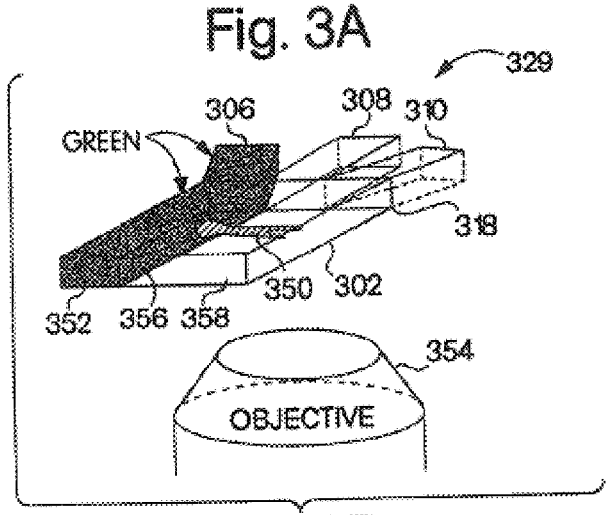
FIG. 3B is an enlarged view of a portion of the microfluidic network of FIG. 3A.

The precise dimensions of the distinct components of a multi-component fluid stream and the position of the interfaces between the components can also be readily determined experimentally, while the device is in operation by, for example, including a material within the fluid streams, for example a dye, fluorescing substance, etc. which makes their size and position within the main flow channel readily detectable, for example, by microscopic observation as shown in FIG. 3B.

In general, for microfluidic networks designed and fabricated as discussed above, the thickness of individual components of a multi-component fluid stream in a main channel of the network and, accordingly, the separation between interfaces separating adjacent components can range anywhere from about 1 micrometer up to a distance approximating the width of the main flow channel. Accordingly, several such components and interfaces can be positioned such that they are in contact with the external surface of a single, typically sized cell.

Referring now to FIG. 1C, region 329 including the portions of the flow channels immediately upstream and downstream of junction 318 is shown in magnified detail. A single cell 340 is shown attached to substrate 320 and positioned in main flow channel 302 such that its external surface is in contact with each of flow components 330, 332, and 334 of the fluid stream, and such that both interfaces 336 and 338 are positioned in contact with the external surface of the cell. Such a configuration could be used, for example, to expose regions 342, 344, and 346 of the cell to different biologically active substances contained within each of the components of the fluid flow, for example in order to localize such substances within the cell in regions proximate to each of the above-mentioned regions of the cell surface, and/or to study the effects of such substances on particular regions of the exterior and/or interior of the cell.

After the inlet streams converge at junction 318 and come into contact with one another in main flow channel 302 (i.e., at interfaces 336 and 338), diffusive mixing will tend to occur at the interfaces, between adjacent components of the stream which differ from each other with respect to the presence of, or bulk concentration of, one or more substances. Diffusive mixing will tend to occur at the interfaces between the flow components and the relative thickness of the diffusive region comprising the interface will have a tendency to grow with time of contact between the components as they flow along the length of main flow channel 302, thus blurring the transition between the bulk properties of the individual components. Accordingly, in preferred embodiments, where it is desired to expose a single cell to two or more flow components with differing bulk properties in order to study differential effects of such bulk properties on the cell and/or utilize the differences in the bulk properties (e.g. a difference in bulk concentration of one or more substances) within the component for creating an intracellular gradient within the cell, it is desirable to maintain the thickness of the interface, and the extent of diffusional broadening at the interface, at value that is small with respect to the cell size.

For this reason, in preferred embodiment, the region of the microfluidic network selected for performing the observation, detection, and/or study of single cells positioned in the multi-component fluid stream is limited to a region less than about 500 micrometers downstream of junction 318 where the fluid streams converge. This distance is selected such that the square root of the average squared net distance traveled by diffusion of substance of interest at the interface (which is essentially equivalent to the effective thickness of the interface and the extent of diffusional broadening) is less than, and preferably substantially less than, the size of the cell under study. For example, for two adjacent aqueous fluids comprising two components of the fluid stream, the first component including a substance of interest having a diffusion coefficient of about $5 \times 10^{-6}$ $cm^2$/s, with the adjacent fluid component being essentially free of the substance, the diffusional broadening of the interface between the two components will increase by about 10 micrometers for every 0.1 seconds of contact. Thus, for an average bulk flow velocity in the main channel of the network system of about 0.5 cm/s over the time of treatment of the cell (a typical value for microfluidic network system 300 having the configuration discussed above), a diffusional broadening of the interface between the flow components of about 10 micrometers will occur by the time the components have flowed to approximately 500 micrometers downstream of junction 318. Accordingly, for embodiments having cell sizes such that 10 micrometers will be a maximum tolerable extent of diffusional broadening of the interface (e.g., for embodiments involving spread cells having a diameters of 50 micrometers or greater), cells for study should be selected within region less than 500 micrometers downstream from the junction point. It should be apparent that for differentially sized cells, substances having different diffusion coefficients than illustrated, different flow rates, etc., the particular area over which diffusional broadening at the interface between components will comprise an acceptably small fraction of the cell size will vary. Estimation of the rate of diffusional broadening can be made by standard techniques well known in the arts of mass transport and fluid mechanics, and with reference to knowledge and information possessed by those of ordinary skill in such arts. Such calculations are described in more detail, for example, in Atkins, P. W. "Physical Chemistry" Freeman, N. Y. (1994), incorporated herein by reference; and Kamholz, A. E., et al., 1999, previously incorporated herein by reference.

FIGS. 3A–B illustrate the use of microfluidic network system 300 for creating a two-component fluid stream in main flow channel 302 for selectively treating a left-hand portion of a cell 350 with a substance of interest. Initially, prior to establishment of the multi-component flow stream, microfluidic network 300 can be treated to facilitate the attachment of cells to cover glass substrate 320 and filled with a suspension of cells to enable cell attachment/binding to the substrate, and spreading thereon. In some embodiments, the microfluidic network channels of microfluidic network 300 may be filled with a desired cell suspension and the cells may be allowed to settle onto an untreated substrate 320 and attach and spread non-specifically. In other embodiments, substrate 320, or the entire microfluidic network of system 300 may be first exposed to or chemically-treated with one or more substances which facilitate non-specific or specific cell attachment spreading, for example, fibronectin.

In addition, in some embodiments, portions of substrate 320 may be differentially treated, for example through utilization of a laminar flow patterning technique such as described in Takayama, S., et al., 1999, in order to form patterned regions of substrate 320 to differentially facilitate cell binding and/or to facilitate selective binding of particular types of cells in particular areas of the microfluidic channel. In this way, the present inventive technique of selectively treating parts of a single cell could be combined with the selective patterning techniques as disclosed in Takayama, S., et al., 1999 in order to facilitate the construction of sensors, assay systems, etc. able to both selectively position desired cells/cell types in particular positions within main channel 302 of the microfluidic network and subsequently selectively position two or more components of a fluid treatment stream, and interfaces therebetween, to pass over and contact selected cells of the patterned arrangement of cells on the substrate, such that, for example, cells of different cell types may be simultaneously or sequentially studied utilizing the single-cell treatment techniques disclosed and provided by the present invention. The combination of selective patterning of cells within the main flow channel 302 and the selective treatment of parts of cells so patterned and positioned within the main flow channel can substantially increase the flexibility and utility of the inventive system for performing single cell studies. Such combination can also enable further study of the presence and relative locations of different cell types with respect to each other, the effect of different substrate binding conditions on cellular behavior/interactions, etc., and a wide variety of other assays, tests, etc. wherein the interaction between different cell types and/or cell types and different substrate environments can be important, as would be apparent to those of ordinary skill in the art.

As illustrated in FIGS. 3A–B, subsequent to preparation of the microfluidic network to facilitate cell binding, for example by immobilization of fibronectin thereto, and subsequent to filling the channels with a cell suspension and allowing cells (e.g., cell 350) to attach and spread on substrate 320, a two-component fluid stream is created by filling inlet well 312 with a fluid containing a green-fluorescing active substance and filling wells 314 and 316 with a similar fluid, except not including the active substance. Outlet well 304 is maintained free of fluid, as shown, to facilitate flow within the microfluidic system established and maintained by a driving force created by the difference in height of the fluids in the inlet wells and the outlet wells.

In the illustrated embodiment, an appropriate cell for study is chosen, and the effect of the treatment with the active substance contained in component 352 of the fluid flow stream in main channel 302 is detected by observing region 329 immediately downstream of junction 318 (e.g., within about 50 to about 500 micrometers downstream of junction 318) utilizing microscope objective 354 and a fluorescent optical filter able to visualize the green fluorescence of the fluid comprising fluid component 352. A cell 350 is then selected for observation and study which is positioned such that interface 356 between component 352 containing the active substance and component 358 of the flow lacking the active substance passes over of a main body portion of the cell. As discussed previously, preferably, cell 350 is selected such that the interface 356, at the position where the cell is located, is sharp and has a minimal amount of diffusional broadening (i.e., cell 350 is positioned in close proximity to junction 318). As discussed in more detail immediately below in the context of FIG. 2, such a cell can be continuously observed via objective 354 of a microscopic optical detection system during a selected treatment time to determine the effect of the active substance in flow component 352 on the cell. In some embodiments, as described below in the context of FIG. 2, the substance supplied to the cell in component 352 is a substance that permeates through the plasma membrane of cell 350 becoming localized within the intracellular space of cell 350 in a region proximate to at least a portion of the portion of the exterior of cell 350 in contact with flow component 352, such that an intracellular gradient of the active substance is established within cell 350.

It should be understood, that in other embodiments the active substance need not be a fluorescing or visually detectable substance. For embodiments where the optical properties of the different components of the fluid stream contacting a single cell are essentially the same, as described previously, an inert dye, compatible with the active substance and non-interfering with the test to be performed, can be added to one or more of the inlet streams in order to create a visual contrast between the different flow components established within the main channel such that an appropriate cell can be selected for study, as described above. In addition, other detection means than the optical microscope illustrated may be utilized, in appropriate situations, to detect active substances and/or changes/responses of the cell to a selected treatment. A wide variety of such detection systems and methods, for example, radioactivity detectors, magnetic resonance detectors, conductivity detectors, etc., are well known to those of ordinary skill in the art and can be utilized within the context and scope of the present invention, as would be apparent to those of ordinary skill in the art.

Figure 2A:
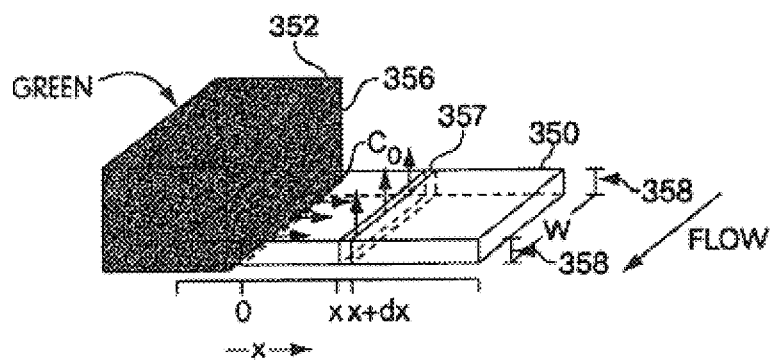
FIG. 2A is a schematic, perspective view of a model cell treated according to one embodiment of the inventive method.
Figure 2B:
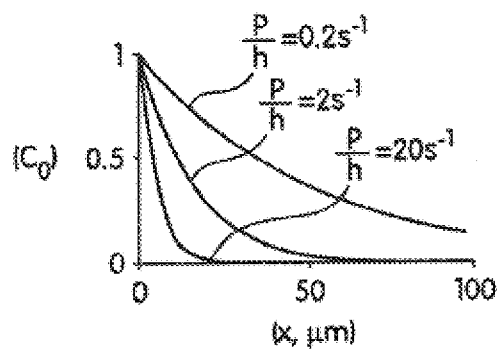
FIG. 2B is a graph of intracellular concentration gradients as a function of position within the model cell of FIG. 2A for various ratios of permeability to cell thickness.
Figure 2C:
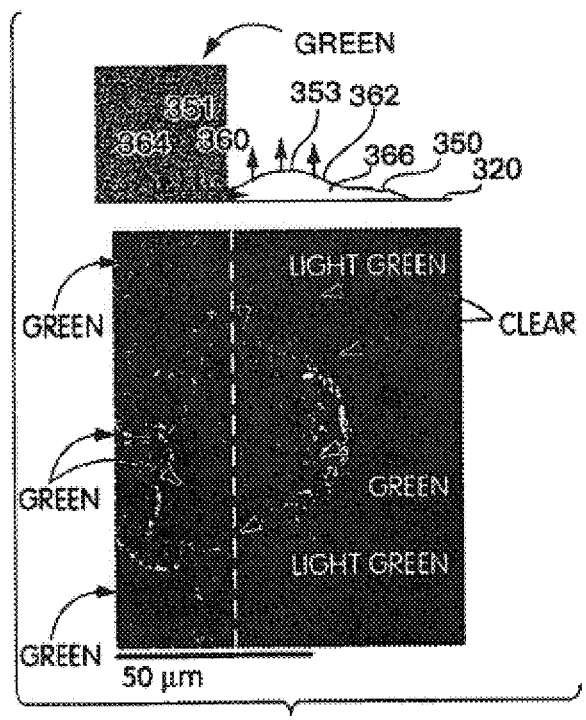
FIG. 2C shows a schematic, cross-sectional view (top) of a cell treated according to one embodiment of the invention, and further shows (bottom) an en face fluorescence photomicrograph of a cell so treated.

FIGS. 2A–C illustrate one embodiment for creating an intracellular gradient of an active substance within cell 350 utilizing microfluidic network 300, as configured and operated in FIGS. 3A–B. In the embodiment illustrated in FIGS. 2A–C, left-most flow component 352 contains a green-fluorescing, cell membrane-permeable small molecule active substance (e.g., a membrane permeable fluorescent dye). The green-fluorescing small molecule active substance included in flow component 352, in the illustrated embodiment, can be a substance that remains freely diffusable within the cell, or that is able to reversibly bind to nucleic acids, or other immobile components, within the cell, such that upon permeating into the cell, a portion of the substance will be freely diffusable within the cell and another portion will be reversibly bound to nucleic acids/immobile structures within the cell (e.g., within the nucleus of the cell). As illustrated, inlet wells 314 and 316 (see FIG. 3A) are filled with a similar buffer/medium, except not including the green-fluorescing active substance, such that a second component 358 of the fluid stream is positioned over cell 350, which component is essentially free of the active substance. Cell 350, as illustrated, has been selected such that interface 356 appears to be very sharp with a minimal amount of diffusional broadening at the interface.

Active substances able to permeate across the cell plasma membrane that are small molecules with a typical diffusion coefficient on the order of about $5 \times 10^{-6}$ cm$^2$/s or more will tend to diffuse within the cell over a length several times the maximum size dimension of a typical cell in a short period of time (e.g., under 1 minute). It is for this reason that typical prior art methods for localizing active substances within cells are unable to create and maintain long-term intracellular gradients. As previously discussed, such prior art techniques for localizing substances within a cell typically result in a redistribution of the material with in the cell such that the substance reaches approximately 95% of its final equilibrium distribution within the cell within a couple of minutes.

By utilizing the techniques provided according to the present invention, for example as illustrated in FIGS. 2A–C, significant intracellular concentration differences between distinct regions of the cell (e.g., concentration differences of greater than 5%) can be maintained for long periods of time, as discussed above, even for substances that are freely diffusable within the cell. The establishment and maintenance of the intracellular concentration gradient in the illustrated embodiment is enabled by providing an influx of the substance to the interior of the cell by supplying the substance to portion 360 of the exterior surface of the cell via contact with flow component 352 (see FIG. 2C top) and removing the substance from exterior surface portion 362 of cell 350 by contacting the portion with flow component 358 during treatment. Such treatment can establish an intracellular gradient characterized by a region 364 within the cell which there is a relatively high concentration in the active substance and a region 366 within the cell where the concentration is lower, and in some instances can be essentially free of the active substance.

The extent, character, and distribution of the active substance within the cell as a function of the physical/biophysical/chemical/biochemical properties of the cell and the properties of the active substance and the design/operating parameters of the microfluidic network performing the single-cell treatment can be estimated, modeled, or predicted using well-known principles of mass transport, or straightforward adaptations thereof, to predict the spatial distribution of active substance within the cell (such well known principles of mass transport are discussed, for example, in Bird, R. B., Stewart, W. E., and Lightfoot, E. N., 1960; Atkins, P. W., et al., 1994; Kamholz, A. E., et al., 1999, each previously referenced and incorporated by reference; and Crank, J., *The Mathematics of Diffusion*, Oxford University Press, Oxford (1975); Blatter, L. A. and Wier, W. G., "Intracellular diffusion, binding, and compartmentalization of the fluorescent calcium indicators indo-1 and fura-2," *Biophys. J.*, Vol. 58, 1491–1499 (1990); and Blum, J. J., Lawler, G., Reed, M., and Shin, I., "Effect of cytoskeletal geometry on intracellular diffusion," *Biophys. J*, Vol. 56, 995–1005 (1989), each incorporated herein by reference.

The illustration, presented below, is a mathematical description, developed by the inventors utilizing the well known principles of mass transport discussed above, of the intracellular concentration gradient generated in a model cell 350, as treated by the conditions illustrated in FIGS. 2A–C (i.e. a rectangular cell attached to an impermeable substrate 320 (FIG. 2C top), having a dimension in the direction of fluid flow (w), an infinite length (x) in the direction perpendicular to fluid flow and a thickness/height (h), which can vary with position (x), and exposed to a flow component 352 containing a bulk concentration (Co) of an evenly distributed membrane-permeable active substance that is freely diffusable within the cell and a flow component 358 that is essentially free of the active substance, with an infinitely thin interface 356 between the components of the flow). The intracellular concentration gradient of the active substance within cell 350 for such conditions can be approximated by Equation 1 below:

$$\frac{\partial c}{\partial t} = D \frac{\partial^2 c}{\partial x^2} - \frac{P}{h} c \qquad \text{Eq. 1}$$

In Equation 1, D (cm$^2$/s) is the diffusion coefficient, c is the concentration of the active substance, P (cm/s) is the permeability constant of the substance across the plasma membrane of the cell, and h (cm) is the height of the cell at a given location x.

For a particular embodiment, as illustrated in FIG. 2A, considering the model cell 350, with a boundary condition of c0=C$_0$ and c$_\infty$=0 (i.e., c at x=0 is always C$_0$ and c at x=$\infty$ is always 0) an analytical solution for the concentration gradient at steady-state $$\left( e.g. \text{ when } \frac{\partial c}{\partial t} = 0 \right)$$

is represented by:

$$c = C_0 e^{-x \sqrt{\frac{P/h}{D}}} \qquad \text{Eq. 2}$$

The above analysis does not rely on any reduction in apparent diffusion rates that may occur by binding of molecules of the active substance to immobile components within the cell or due to geometric barriers.

Equation 1 can be derived by considering the volume element whdx (357) shown in FIG. 2A. The rate of entry of molecules of active substance into this volume element by intracellular diffusion is represented by:

$$-D \frac{\partial c}{\partial x} wh \qquad \text{Eq. 3}$$

The rate of removal of molecules of active substance from this volume element through intracellular diffusion (in the direction of the horizontal arrows) and by efflux of molecules out of cell through permeation through the plasma membrane is represented by:

$$-D \left( \frac{\partial c}{\partial x} + \frac{\partial^2 c}{\partial x^2} dx \right) wh + Pcwdx \qquad \text{Eq. 4}$$

The rate of accumulation of molecules of the active substance in this volume element, which is the difference of the two previous terms is given by:

$$D\frac{\partial^2 c}{\partial x^2} whdx - Pcwdx \qquad \text{Eq. 5}$$

The rate of change of concentration $$\left(\frac{\partial c}{\partial t}\right)$$

(i.e., the rate of accumulation/volume (whdx)) is given by the expression shown above as Eq. 1.

With a boundary condition of $c_0 = C_0$ and $c_{2s} = 0$, one can also obtain an analytical solution for the development of the concentration profile within the cell as a function of time prior to steady state:

$$c = \frac{1}{2} C_0 e^{-x\sqrt{P/h}{D}} \operatorname{erfc}\left[\frac{x}{2\sqrt{Dt}} - \sqrt{\frac{P}{h}}t\right] + \qquad \text{Eq. 6}$$

$$\frac{1}{2} C_0 e^{x\sqrt{\frac{P/h}{d}}} \operatorname{erfc}\left[\frac{x}{2\sqrt{Dt}} + \sqrt{\frac{P}{h}}t\right]$$

Using this equation, the time required for the concentration gradient to reach more than 90% of its steady-state value was calculated to be less than about 10 seconds for $D=5\times 10^{-6}\ cm^2/s$ at P/h values ranging between about 0.2–200 $s^{-1}$.

FIG. 2B illustrates calculated results using the above equations for steady-state intracellular concentration gradients of a typical rapidly diffusing small molecule active substance ($D=5\times 10^{-6}\ cm^2/s$) for model cell 350 for several values of P/h. These calculated results illustrate the general applicability of the inventive techniques for establishing steady-state intracellular gradients and subcellular localization of small molecule active substances having a wide range of permeabilities (P) in surface attached cells, such as model cell 350 in FIG. 2A, although with different degrees of spatial resolution and degrees of difference in concentration between regions of maximum and minimum concentration within the cell depending on the permeability of the active substance (i.e., the higher the permeability (P) the greater the difference). For example, in an exemplary embodiment involving a spread cell with a height of about 5 $\mu$m (many types of attached and spread mammalian cells have a maximum cell height of ~5 $\mu$m) the above calculated results illustrate the applicability of the inventive techniques for establishing steady-state intracellular gradients and subcellular localization of small molecule active substances having permeabilities ranging at least within the range of about 1 to about $10^{-4}$ cm/s. As the as the height of the cell is decreased (e.g. below 5 $\mu$m), the permeability of the active substance required to successfully form the above-described long-term or steady state intracellular gradients will also be decreased over the above-mentioned range (see FIG. 2B), and, for some such thin spread cells, the inventive techniques for a establishing steady-state intracellular gradients and subcellular localization of small molecule active substances could be successfully employed for forming such gradients of active substances having permeabilities ranging down, from the above-mentioned range, to about $10^{-8}$ cm/s or less. In general, areas of high concentrations of small molecule active substances can be spatially confined in the cell with greater resolution with increasing permeability, decreasing thickness of the cell, and decreasing diffusion coefficient.

Equation 2 above can be used together with an observation or detection of the concentration distribution of the active substance in the x direction within the cell to determine a measurement related to the relative height of the cell at the selected position and to determine a measurement related to the permeability of the active substance through the cell plasma membrane. In the embodiment illustrated in FIG. 2, such measurement can be made by determining, quantitatively, the fluorescence intensity within the cell as a function of distance x.

Referring to Eq. 2 at constant c, the relationship between intracellular diffusion distance x at the point of constant c, and height h of the cell indicates that:

$$x \propto \sqrt{h} \qquad \text{Eq. 7}$$

Similarly, at constant c:

$$x \propto \sqrt{\frac{1}{P}} \qquad \text{Eq. 8}$$

Thus, the inventive method can be utilized to determine the relative height of a spread cell above the substrate at various locations and to compare the relative permeabilities of various active substances across the cell membrane, or to study the effects of various cell treatments on the permeability of the cell membrane to a given active substance, with the analysis and technique described above.

For an embodiment where the active substance can reversibly bind components that are immobile within the cell within the time-scale of the experiment, such that not all of the substance is freely diffusable within the cell at any given time, the relationships between x and h of Eq. 7 and x and P of Eq. 8 are still valid at steady-state. To illustrate, if the concentration of bound molecules is S, then Eq. 1 becomes:

$$\frac{\partial c}{\partial t} = D\frac{\partial^2 c}{\partial x^2} - \frac{P}{h}c - \frac{\partial S}{\partial t} \qquad \text{Eq. 9}$$

which has a steady-state solution that is still given by Eq. 2. Furthermore, since $S \propto c$ c, then Eq. 7 and Eq. 8 are still valid, even for the portion of active substance molecules which become bound and immobilized within the cell.

In addition to the above-described applications using the inventive techniques for contacting a cell with two or more fluids or components of a fluid stream, where one fluid or component of the stream has a different potential to carry out a biophysical or biochemical interaction at a portion of the cell in which it is in contact then the other fluid or component of a fluid stream, the inventive techniques are also useful for selectively carrying out biophysical or biochemical interactions at portions of the cell that are proximate to and in contact with interfacial boundaries (e.g. boundaries 336 and 338 illustrated in FIG. 1) between fluids or fluid stream components. In certain preferred embodiments, such biophysical or biochemical interactions occurring proximate to an interface between fluids or fluid stream components is enabled by positioning adjacent fluids or components of a fluid stream next to and in contact with one another, where one of the fluids/components includes a substance which acts as a first reactant, and a second adjacent fluid/component includes a substance which acts as a second reactant, such that in the boundary or interfacial region where diffusive mixing occurs, a chemical reaction takes place between the first reactant and the second reactant producing a product substance able to effect a biophysical or biochemical interaction at the portion of the cell in which the interface is in contact.

Referring to FIG. 1C, in one such embodiment, fluid stream component 330 can include therein a water soluble carbodiimide, while component 332 of the fluid stream contains an amine or carboxylate and N-hydroxysuccinimide. In such an embodiment, a chemical reaction will occur at interface 336 between components 330 and 332 of the fluid stream, forming a reaction product able to label cell 340 at the position of the interface.

In other useful embodiments employing a reaction at an interface between fluids/components of a fluid stream, delivery of nitric oxide, as a reaction product produced at the interface, to a portion of cell proximate to the interface between the two fluids/components can occur. Again referring to FIG. 1C, in a first embodiment, fluid component 330 can contain arginine and molecular oxygen, while fluid component 332 contains nitric oxide synthase. In another embodiment, component 330 of the fluid stream is an alkaline media having pH above about 8, with component 332 of the fluid stream including dissolved therein N-(N'-acetylphenylalanylmethylenyloxy)-N-phenyldiimide N-oxide. In yet another embodiment for forming interfacial nitric oxide, component 330 of the fluid stream contains chymotrypsin, while component 332 of the fluid stream contains N-(N'-acetylphenylalanylmethylenyloxy)-N-phenyldiimide N-oxide. In yet another embodiment for forming interfacial nitric oxide component 330 of the fluid stream is a media containing thiols, while component 332 of the fluid stream includes 3-halogeno-3, 4-dihydrodiazete 1, 2-dioxides. In addition to the above-described examples, those of ordinary skill in the art will readily envision a variety of other systems for performing a reaction in an interface, which interface is positioned over a single cell, for creating, studying, analyzing, etc. useful biochemical or biophysical interactions carried out on the cell by the products of the interfacial reaction.

The function and advantage of these and other embodiments of the present invention will be more fully understood from the examples below. The following examples are intended to illustrate the benefits of the present invention, but do not exemplify the full scope of the invention.

EXAMPLES

Example 1
Formation of an Intracellular Gradient of a DNA/RNA Binding Agent and Measurement of a Relative Thickness of a Cell at a Particular Location by Measuring the Extent of the Intracellular Diffusion a. Device Fabrication A negative relief of poly(dimethylsiloxane) (PDMS) was formed by curing a prepolymer (Sylgard 184, Dow-Corning) on a silanized silicon (Si) master having a positive relief of the capillary channels formed in photoresist (SU-8-50, MicroChem) on its surface by a replica molding method as described in Duffy, D. C., et al., 1998, and Takayama, S., et al., 1999, both previously incorporated herein by reference. The PDMS membrane 301 thus formed, with a negative relief microchannel system, was placed on a microscope cover glass 320 resulting in the formation of capillary channels able to act as flow channels for fluid. The PDMS membrane sealed against the glass microscope cover glass by conformal contact, without the need to make the PDMS hydrophilic by plasma oxidation or other methods before use. The resulting microchannel system 300 (as shown in FIG. 3A) had a main flow channel 302 in fluid communication with an outlet well 304 and three feed channels 306, 308, 310, fed by inlet wells 312, 314, and 316, respectively. The feed channels converged into main flow channel 302 at junction 318. Each of the channels was about 300 $\mu$m in width and about 50 $\mu$m in depth.

b. Cell Culture and Attachment

Bovine adrenal capillary endothelial (BCE) cells were cultured and harvested as described in D. E. Ingber & J. Folkman, *J. Cell Biol.*, Vol. 109, pp. 317–330, 1989, incorporated herein by reference. In brief, cells were cultured under 10% $CO_2$ on Petri dishes (Falcon) coated with gelatin in DMEM (GIBCO) containing 10% calf serum (CS), 2 mM glutamine, 100 $\mu$g/ml streptomycin, 100 $\mu$g/ml penicillin, and 1 ng/ml basic fibroblast growth factor (bFGF). Cells were dissociated from culture plates with trypsin/EDTA and washed in DMEM containing 1% wt/vol BSA (BSA/DMEM). These cells were suspended in chemically defined medium (10 $\mu$g/ml high density lipoprotein/5 $\mu$g/ml transferrin/5 ng/ml bFGF in BSA/DMEM) as described in D. E. Ingber, *Proc. Natl. Acad. Sci. USA,* Vol. 87, pp. 3579–3583 (1990), incorporated herein by reference, introduced into capillary networks (pretreated with 50 $\mu$g/ml fibronectin for 1 hr) from the inlet wells, and incubated in 10% $CO_2$ $_{at}$ 37° C. for 4–6 hr to permit attachment and spreading upon the glass cover slip forming the bottom of the microchannel network. After the above incubation to allow for binding and attachment, non-adherent cells were removed by washing each of the flow channels with media (1% wt/vol. BSA/DMEM) for about 3 min. at a maximum bulk flow velocity of about 0.6 cm/s (Re<1).

c. Intracellular Gradient Formation

Inlet well 312 was then filled with a solution of a membrane permeable fluorescent nucleic acid binding dye-Syto 9 (60 $\mu$M in DMEM/10% CS, Molecular Probes). Inlet wells 314 and 316 were filled with a similar solution, but without the Syto 9. Fluid in outlet well 304 was aspirated at regular intervals to maintain a difference in hydraulic head driving the flow in the channels.

The flowing streams and attached BCEs were visualized utilizing a fluorescence inverted microscope, as illustrated in FIG. 3B. A cell was chosen for observation which was positioned such that the interface separating the first component of the flow in the main channel, which included the Syto 9 and appeared fluorescent green under the microscope, and the second, clear, Syto 9-free component was sharp and positioned over the main body portion of the cell (see FIG. 2C, where the interface position corresponds approximately to dashed white line). The cell was selected so that it was positioned less than about 500 $\mu$m from junction 318, in order to minimize the thickness of the region of interface between the two stream components where a diffusion-induced gradient of Syto 9 exists external of the cell.

Flow was maintained until intracellular diffusion reached approximately its steady state value (about 10 minutes). FIG. 2C (bottom) shows a fluorescence photomicrograph illustrating the appearance of the observed BCE cell at steady state. The schematic cross-sectional view of the cell directly above the photomicrograph (FIG. 2C (top)) illustrates the relative thickness of the cell in the different regions of flow as well as the direction of net migration of Syto 9 within the cell and between the cell and the external media (arrows). As expected from the above-described theoretical analysis (i.e. the relationship x $\propto \sqrt{h}$ developed above in Eq. 7) the distance from the laminar flow boundary of Syto 9-containing media (dotted line) to the intracellular migration front (right-most extent of the fluorescent green are within the cell) is greater in the thicker parts of the cell 353 compared to the thinner parts 351.

Example 2
Generation of Two Spatially Localized Populations of Mitochondria within a Single BCE Cell using Different Fluorophores Device fabrication and cell culture and attachment of BCE cells was performed as described above in Example 1. Creation and maintenance of flow in the channels and selection and observation of a BCE cell positioned straddling the interface of two components of the flow stream established in the main flow channel 302 (FIG. 3A) was performed in a similar fashion as described previously in Example 1.

Figure 4A:
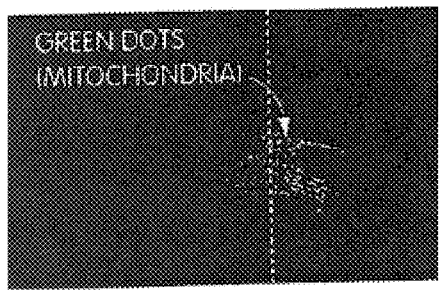
FIG. 4A is an en face fluorescence photomicrograph of a cell after selectively staining mitochondria in a right-hand region of the cell, according to one embodiment of the invention.

At the outset of the experiment, right-most inlet wells 316 of the channel system (see FIG. 3A) was filled with a solution of a membrane-permeable, green-fluorescent mitochondria-specific dye (Mitotracker Green™ FM, Molecular Probes, 3 $\mu$M in DMEM/10% CS), which was allowed to flow over the right portion of the observed BCE cell, while a similar media, except excluding the Mitotracker Green™ FM dye, was added to inlet wells 312 and 314 and allowed to flow over the left portion of the observed BCE cell for 5 min. The channels were then briefly washed with dye-free media and a photomicrograph (with 488 nm excitation, FITC filter) (FIG. 4A) was taken of the BCE cell. The white dotted line in FIG. 4A indicates the position of the interface between the component of the flow essentially free of the fluorescent dye (left) and the component of the flow containing the Mitotracker Green™ FM dye (right).

Figure 4B:
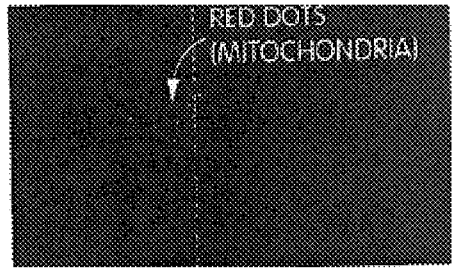
FIG. 4B is an en face fluorescence photomicrograph of the cell in FIG. 4A after selectively staining mitochondria in a left-hand region of the cell.

Subsequently, a solution of membrane-permeable Mitotracker Red™ CM-H$_2$XRos (Molecular Probes, 3 $\mu$M in DMEM/10% CS) was allowed to flow over the left portion of the cell and dye-free media (DMEM/10% CS) was allowed to flow over the right portion of the cell for 1 min. by performing essentially the same flow procedure as described directly above, except adding the Mitotracker Red™ solution to inlet well 312 and dye-free media to inlet wells 314 and 316. The channels were then briefly washed with dye-free media, as described above, and a fluorescence photomicrograph (with 560 nm excitation, TRITC filter) was taken of the cell (FIG. 4B). Again, the white dotted line in the figure indicates the position of the interface between the dye-containing and dye-free components of the flow stream over the cell.

Figure 4C:
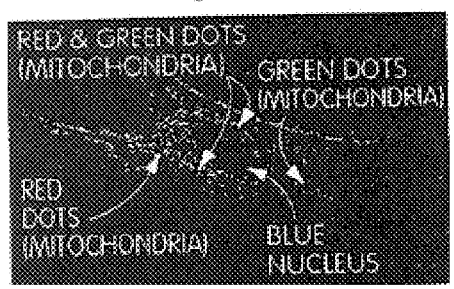
FIG. 4C is an overlay of an en face fluorescence photomicrograph and a phase-contrast photomicrograph of the cell in FIG. 4B showing differently stained mitochondria in the right- and left-hand regions of the cell shortly after selectively staining the mitochondria.

The entire cell was then subsequently washed with media containing a membrane-permeable fluorescent blue nucleus-staining dye (Hoechst 33342, Molecular Probes, 10 $\mu$g/ml in DMEM/10% CS). The cell was then briefly washed with dye-free media, as described above, and observed with the fluorescence microscope. FIG. 4C is a photomicrograph showing an overlay of the BCE cell as observed with the 488 nm excitation, FITC filter (green), the 560 nm excitation, TRITC filter (red), and an optical filter for visualizing the Hoechst 33342 dye (blue), together with a phase contrast image of the cell. Notice that the red stained mitochondria are preferentially segregated in the left-hand portion of the cell and the green stained mitochondria are segregated in the right-hand portion of the cell.

Figure 4D:
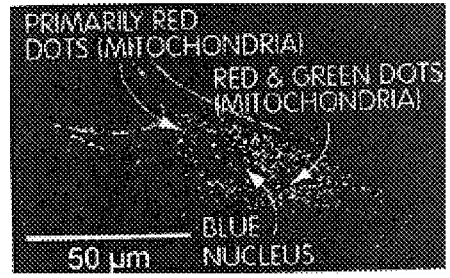
FIG. 4D is an overlay of an en face fluorescence photomicrograph and a phase-contrast photomicrograph of the cell in FIG. 4C taken after allowing time for the mitochondria to redistribute.

FIG. 4D is a photomicrograph illustrating an overlay of the above-described fluorescence and phase contrast images except taken 2.5 hrs. after the selective treatment of parts of the cell with the fluorescent mitochondrial stains, as described above. The image shows that the mitochondria have redistributed significantly towards the right-hand side of the cell, in the direction of migration of the cell on the substrate (as evidenced by the pseudopodia visible at the far right extremity of the cell). The image shows that the left-hand region of the cell after 2.5 hrs. of incubation was still occupied primarily by red-labeled mitochondria, while the right-hand region of the cell contained both red- and green-labeled mitochondria. This observation indicates that the mitochondria have redistributed towards the right, towards the pseudopodia. Because mitochondria in distinct regions of the cell were labeled with different fluorescent labels by the above-described process, the observation of the overall dynamics of mitochondria movement was substantially improved over typical prior art techniques of observing mitochondria with homogenous labeling.

Example 3

Disruption of Actin Filaments and Displacement of Mitochondria Induced by Treatment of a Single BCE Cell with a Membrane-Permeable Actin Disrupting Drug Device fabrication and cell culture and attachment of BCE cells was performed as described above in Example 1. Creation and maintenance of flow in the channels and selection and observation of a BCE cell positioned straddling the interface of two components of the flow stream established in the main flow channel was performed in a similar fashion as described previously in Example 1.

In the present example, prior to selective treatment of a portion of a single BCE cell with a membrane-permeable actin disrupting drug, the BCE cells attached to the microfluidic network were uniformly exposed to media containing Mitotracker Green™ FM mitochondrial stain, as described in Example 2, in order to uniformly stain the mitochondria of each of the BCE cells in the microfluidic channels. Subsequent to mitochondrial staining, partial cell treatment with the actin disrupting drug was accomplished by filling right-most well 316 (see FIG. 3A) of the microfluidic channel network with media containing latrunculin A (1 $\mu$M in DMEM/10% CS). Similar media, except not including the latrunculin A, was added to inlet wells 312 and 314, and flow was maintained during the experiment as described previously in Example 1. Because the latrunculin A-containing media is non-fluorescent and visually transparent, in order to determine the position of the interface between the latrunculin A-containing component and latrunculin A-free component of the fluid flow in main flow channel 302, a small amount of Dextran 70,000-Cascade Blue (0.5 mg/ml, Molecular Probes) was added to the latrunculin A-containing media so that the media would appear blue when viewed with bright field and phase contrast microscopy.

Figures 5A, 5B, 5C, 5D, 5E, 5F:
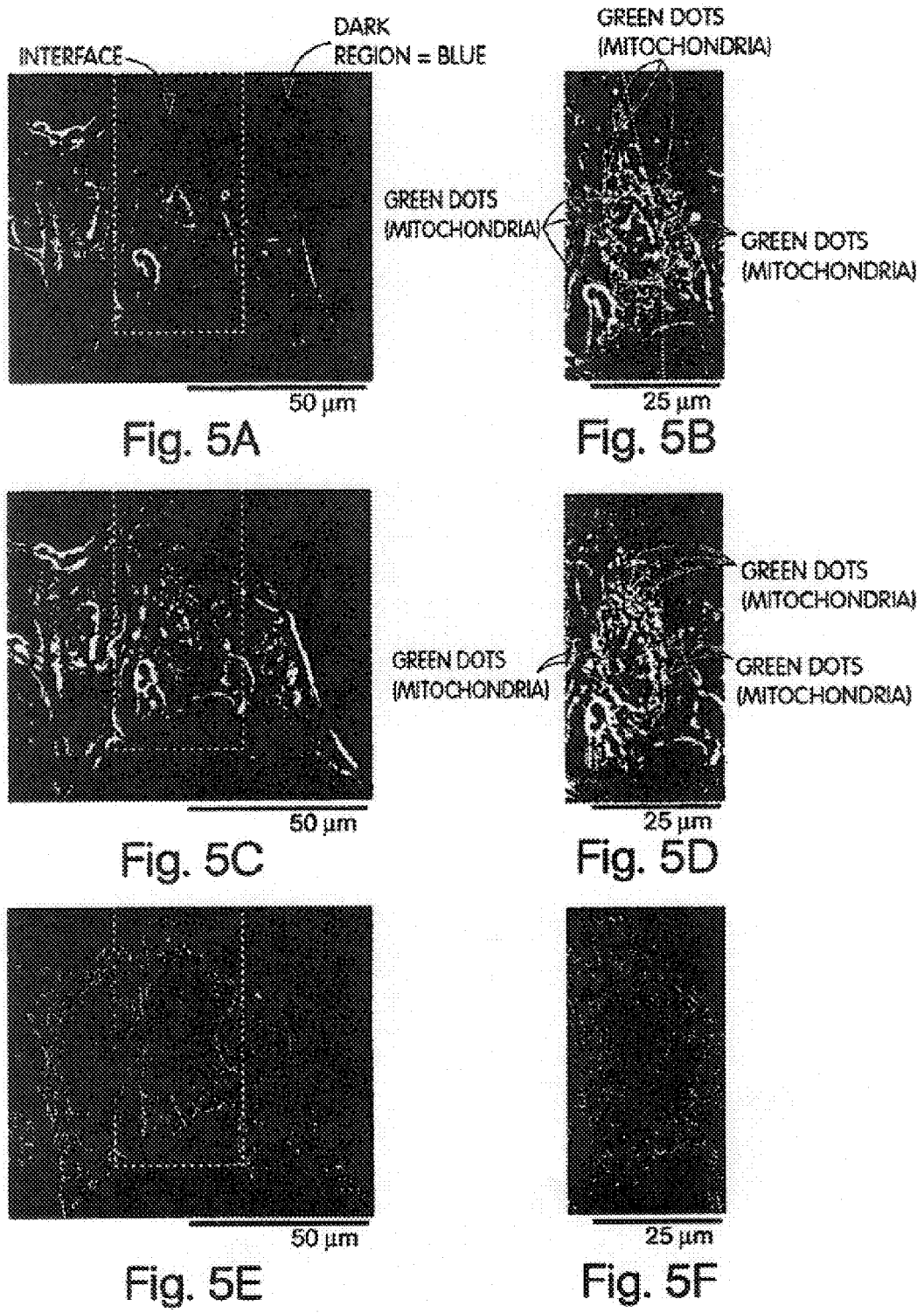
FIG. 5A is an overlay of an en face fluorescence photomicrograph and a phase-contrast photomicrograph of three cells at the commencement of selectively treating the cells with an actin disrupting agent, according to one embodiment of the invention.
FIG. 5B is an overlay of an en face fluorescence photomicrograph and a phase-contrast photomicrograph of the center cell in FIG. 5A.
FIG. 5C is a phase-contrast photomicrograph the three cells of FIG. 5A after completion of selectively treating the cells with the actin disrupting agent.
FIG. 5D is an overlay of an en face fluorescence photomicrograph and a phase-contrast photomicrograph of the center cell in FIG. 5C.
FIG. 5E is an en face fluorescence photomicrograph of the three cells in FIG. 5C, after fixation and staining of the cytoskeleton of the cells.
FIG. 5F is an en face fluorescence photomicrograph of the center cell in FIG. 5E.

FIG. 5A is a phase-contrast photomicrograph of three BCE cells selected for observation at the beginning of the latrunculin A treatment. The blue region (right) represents the flow of media containing latrunculin A and Dextran 70,000-Cascade Blue. As can be seen from the figure, the interface between the latrunculin A-containing component of the flow stream and the latrunculin A-free component of the flow stream was positioned over the center cell.

FIG. 5B is an overlay of fluorescence and phase-contrast images of the center cell in FIG. 5A. The image shows an enlarged view of the center cell in phase contrast, overlaid with a fluorescence photomicrograph showing its green-stained mitochondria. The position of the interface between the above-mentioned two components of the flow stream is shown by the dotted white line.

FIG. 5C shows the same cells as shown in FIG. 5A, except after exposure to the two-component flow stream for a period of about 10 min. FIG. 5D is an enlarged view of the center cell of FIG. 5C in phase contrast, overlaid with a fluorescence photomicrograph of its mitochondria (stained green). Comparison of FIGS. 5D and 5B indicates that the positions of the mitochondria, after exposure of the right-hand part of the cell to latrunculin A-containing media for 10 min., have shifted towards the left-hand (untreated) part of the cell.

FIG. 5E is a fluorescence photomicrograph of the same three cells as shown in FIG. 5C, after the above-described treatment with latrunculin A, and subsequent to fixation and staining of the actin cytoskeleton (with phalloidin Alexa 594, Molecular probes—Cells fixed with 4% formaldehyde in phosphate buffered saline (PBS) for 15 min., followed by permeabilization of the membrane with 0.2% Triton X-100 for 2 minutes, followed by incubation with the stain and washing with PBS). FIG. 5E shows that the actin cytoskeleton is largely intact in the left cell, which was not exposed to the latrunculin A. In contrast, a substantial portion of the actin cytoskeleton appears, in the rightmost cell, to be depolymerized. The center cell (shown most clearly in FIG. 5F), which was partially exposed to the latrunculin A-containing media, as described above, has the greatest degree of actin disruption evident in its treated, right side portion, which portion also corresponds to the region showing the largest displacement of mitochondria (as shown in FIG. 5D above).

Thus, the present example demonstrates the ability of the inventive method to selectively disrupt actin filaments in only part of a cell. Cytoskeletal architecture is important for mechanotransduction within cells. Previously, studies of the mechanical properties of the cytoskeleton of cells have typically used methods that either stress the cell mechanically and locally, or that disrupt the cytoskeleton indiscriminately throughout the entire cell. Unlike the present invention, as exemplified in this example, typical prior art methods are not able to disrupt the cytoskeleton in only a portion of a single cell via use of cytoskeletal-disrupting chemicals.

As shown in FIG. 5D, disruption of the actin filaments in the right-hand region of the center cell by selectively supplying latrunculin A-containing media to the right-hand portion of the cell caused the mitochondria and nucleus to shift towards the left, even though the overall peripheral shape of the cell remained relatively unchanged. This observation is in accord with suggestions in the prior art that the cytoskeleton of a cell comprises a tensegrity structure in which actin filaments are the tensile elements and microtubules act as struts. The observed displacement of the mitochondria, which are mainly associated with microtubules, by local disruption of actin within a portion of the cell is consistent with, and demonstrative of, this suggested mechanism.

Example 4
Demonstration of Intracellular Transport of Cell-Surface Labeled Receptors in a Part of a BCE Cell with Lectin Conjugated to Different Fluorescent Markers Device fabrication and cell culture and attachment of BCE cells was performed as described above in Example 1. Creation and maintenance of flow in the channels and selection and observation of a BCE cell positioned straddling the interface of two components of the flow stream established in the main flow channel was performed in a similar fashion as described previously in Example 1. A portion of a selected BCE cell was selectively treated by establishing the interface between a two-component flowing stream over the cell as described in the previous examples.

Figure 6A:
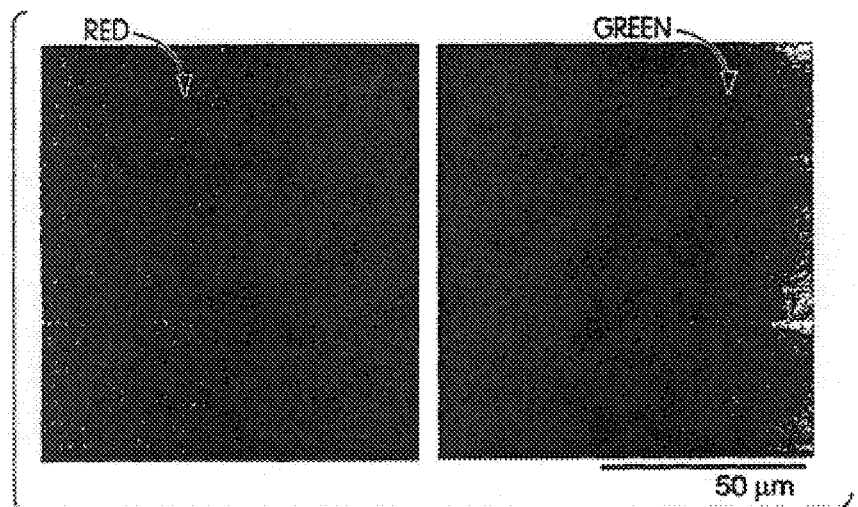
FIG. 6A shows en face fluorescence photomicrographs of left and right fluid stream components each including a fluorescently labeled lectin for treatment of a single cell according to one embodiment of the invention.
Figure 6B:
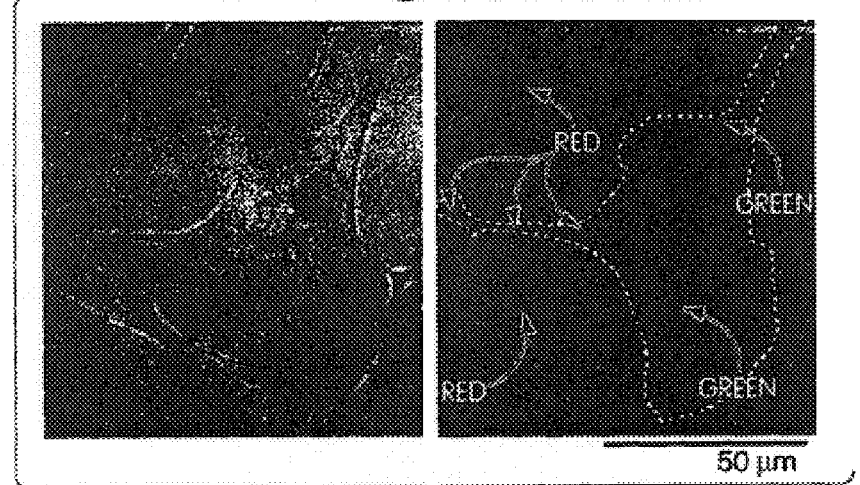
FIG. 6B shows a phase contrast photomicrograph and an en face fluorescence photomicrograph of a cell shortly after treatment with the fluid stream components including labeled lectins, as shown in FIG. 6A.
Figure 6C:
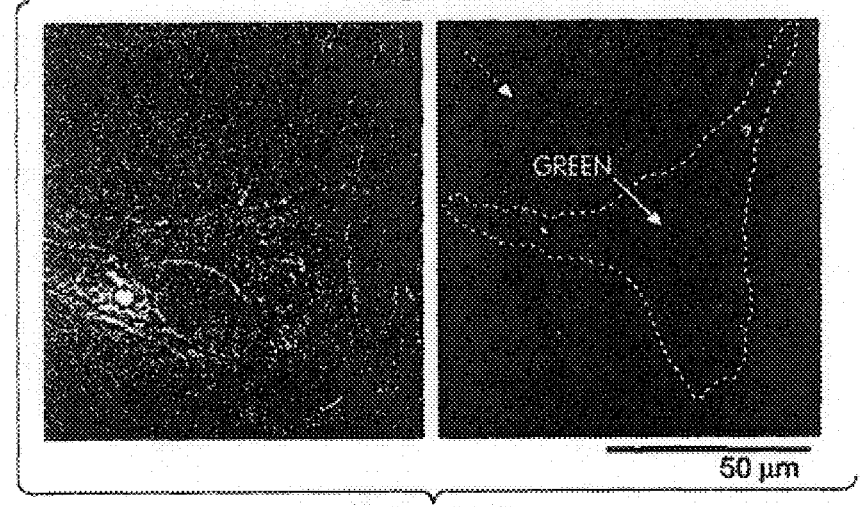
FIG. 6C shows a phase contrast photomicrograph and an en face fluorescence photomicrograph of the cell shown in FIG. 6B, except taken 3 hours later.

FIGS. 6A–C illustrate the results of the area-selective treatment of the cell surface of a BCE cell with fluorescently labeled wheat germ agglutinin (WGA). In the first step, media containing WGA labeled with Texas Red (TRITC-WGA, Sigma, 0.5 mg/ml in DMEM/1% BSA) was allowed to flow over the left-hand portion of a BCE cell for 5 min. (flow stream shown by the fluorescence photomicrograph of FIG. 6A (left)); and in the second step, media containing WGA labeled with Alexa 488 (Alexa 488-WGA, Molecular Probes, 0.5 mg/ml in DMEM/1% BSA) was allowed to flow over the right-hand region of the same BCE cell for 5 min (flow stream shown by the fluorescence photomicrograph of FIG. 6A (right) position of BCE cell shown by phase contrast image FIG. 6B(left)). This procedure resulted in the generation of two differentially labeled populations of cell surface glycoproteins (FIG. 6B (right)). FIG. 6B (right) is an overlay of false colored fluorescence photomicrographs taken with a fluorescein (green) filter and a rhodamine (red) filter. White dotted lines represent the periphery of the cell as seen in the phase contrast image (FIG. 6B(left)). WGA also bound to glycoproteins that were adsorbed to the channel floor, allowing visualization of the regions of the substrate over which the WGA-containing solutions had been allowed to flow (as shown by stained regions of FIG. 6B (right) external to the cells).

FIG. 6C shows photomicrographs of the same region shown in FIG. 6B, except taken 3 hrs. after treatment. The labeled cell surface glycoproteins were transported within the cell; this is most obvious in the perinuclear regions (see solid arrow in FIG. 6C (right)) where there had been no fluorescence previously. Cell movement can be observed by comparing the two phase contrast images in FIGS. 6B and 6C, and also by the presence of non-fluorescent "tracks" left by migrating cells (for example, see dotted arrow in FIG. 6C (right)); attached cells inhibited the WGA solution from labeling the substrate surface to which the cells adhered (darker region in FIG. 6C (right) pointed out by the dotted arrow).

Example 5
Area-Selective Delivery of Fluorescently-Labeled Low Density Lipoprotein (LDL) to a Restricted Portion of a Cell Surface Device fabrication and cell culture and attachment of BCE cells was performed as described above in Example 1. Creation and maintenance of flow in the channels and selection and observation of a BCE cell positioned straddling the interface of two components of the flow stream established in the main flow channel was performed in a similar fashion as described previously in Example 1. A portion of a selected BCE cell was selectively treated by establishing the interface between a two-component flowing stream over the cell as described in the previous examples.

Figure 7A:
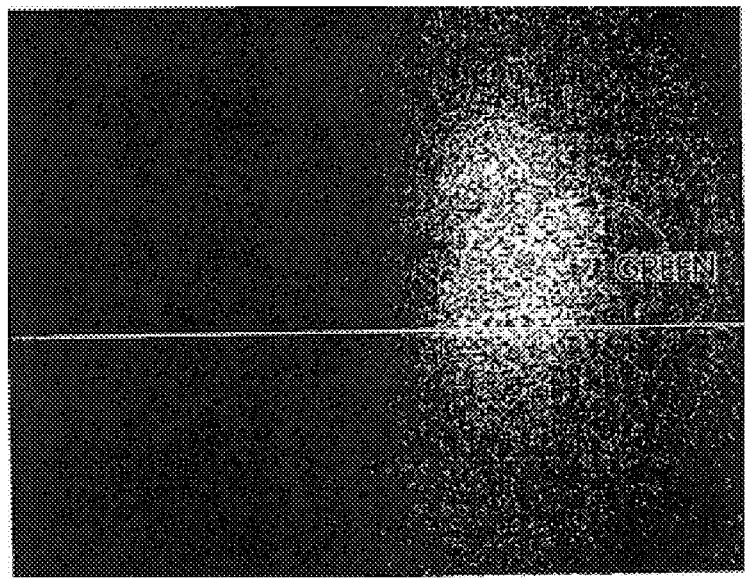
FIG. 7A is an en face fluorescence photomicrograph of left and right fluid stream components, the right component including a fluorescently labeled lipoprotein for treatment of a single cell according to one embodiment of the invention.
Figure 7B:
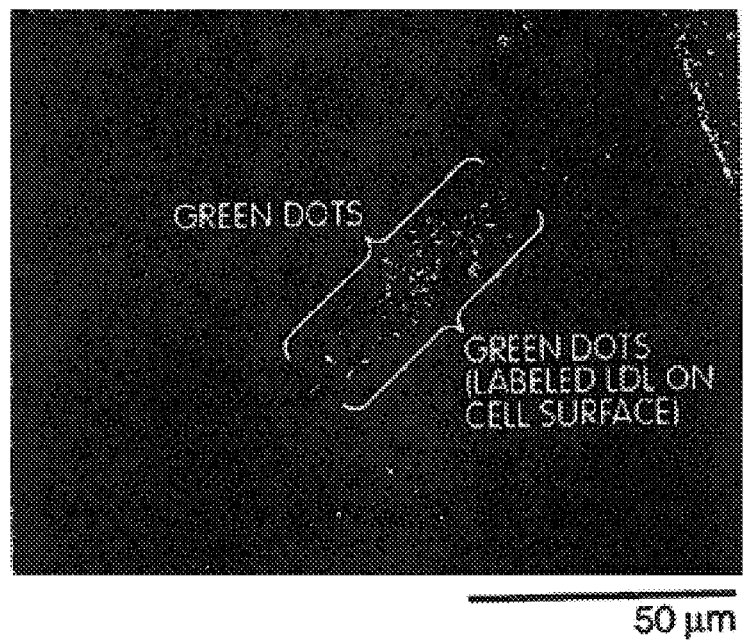
FIG. 7B is an overlay of an en face fluorescence photomicrograph and a phase-contrast photomicrograph of a cell exposed to the fluid stream shown in FIG. 7A, showing differently labeled right- and left-hand regions of the cell plasma membrane.

FIGS. 7A–B illustrate the results of the area-selective delivery of fluorescently labeled acetylated low-density lipoprotein (Ac-LDL) to a portion of the cell surface. Two components of a media stream were allowed to flow over defined regions of an observed BCE cell, one component of the stream containing DiI-Ac-LDL (1, 1'-dioctadecyl-3, 3, 3', 3'-tetramethylindocarbocyanine perchlorate, Molecular Probes) and the other component lacking the labeled LDL for 5 min. (50 $\mu$g/mL in $CO_2$ Independent media (GIBCO) with 10% CS and GPS (Glutamine/Penicillin/Streptomycin mixture).

FIG. 7A is a false colored fluorescence image of the flow of the DiI-Ac-LDL-containing component of the stream (right, green) and the adjacent, LDL-free component of the stream (left). This procedure delivered DiI-Ac-LDL for binding to receptors on a select region of the cell surface. The results of the area-selective binding to the receptors of the cell surface are shown in FIG. 7B, which is an overlay of a phase contrast image and a fluorescence photomicrograph of the cell immediately after treatment. Note that essentially all of the labeled receptors are located on the right-hand side of the main body of the cell, which was the portion exposed to the component of the stream containing the DiI Ac-LDL.

Prophetic Example 1
Simultaneously Delivering Three Differently Labeled Wheat Germ Agglutinins (WGAs) to Selected Areas of a Single Cell Surface Device fabrication and cell culture and attachment of BCE cells is performed as described above in Example 1.

Figure 8:
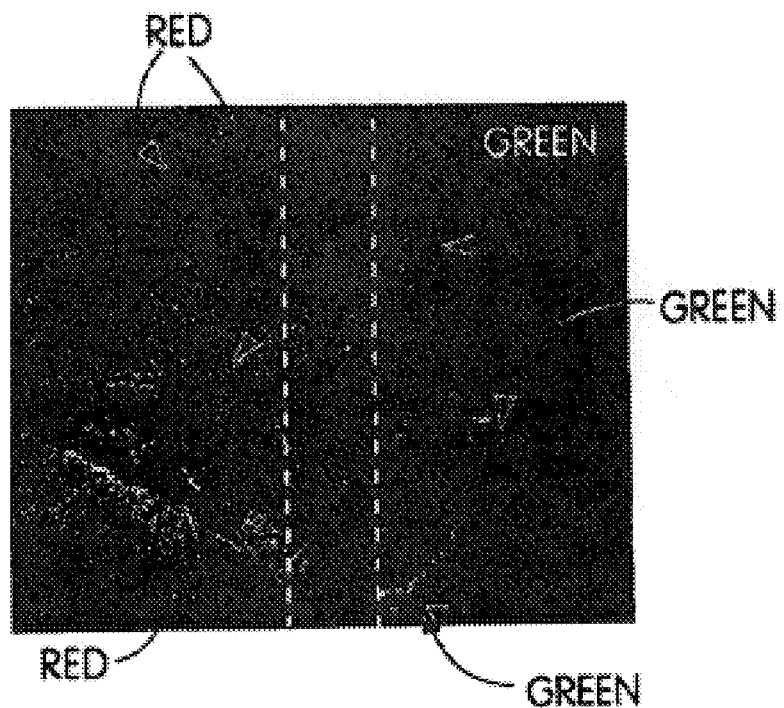
FIG. 8 is an overlay of an en face fluorescence photomicrograph and a phase-contrast photomicrograph of a cell having three differently treated regions thereof, treated according to one embodiment of the invention.

After attachment and spreading of the BCE cells within the microfluidic channels, inlet well 312 (see FIG. 3A) is filled with a solution of WGA labeled with tetramethyl-rhodamine (TRITC-WGA, 0.5 mg/mL in DMEM/1% BSA). Inlet well 314 is filled with the same media, except containing an unlabeled WGA, and inlet well 316 is filled with a solution of WGA labeled with an Alexa 488 fluorescent label (0.5 mg/mL in DMEM/1% BSA). Flow is established through main flow channel 302, and the flow channel is observed with an inverted, fluorescence microscope with appropriate optical filters for observing the red fluorescence of the TRITC-WGA and the green fluorescence of the Alexa 488-WGA. Upon initiation of flow, the region within about 500 μm downstream of junction 318 of the microfluidic network is observed with the microscope, and an appropriate BCE cell is selected, such that the cell includes a first, left-most region in contact with the TRITC-WGA-containing component of the flow stream, a center region in contact with the label-free WGA-containing media, and a right-most region in contact with the Alexa 488-WGA-containing media. The flow, as described, is maintained in contact with the BCE cell for about 5 min. The BCE cell can then, optionally, be washed with a WGA-free media. An overlay of fluorescence and phase contrast photomicrographs of the BCE cell treated as described above shows a cell surface expected to be labeled similarly to that illustrated in FIG. 8, having a left-hand portion to which is bound red TRITC-WGA, a right-hand portion to which is bound green Alexa 488-WGA, and a central portion (between the dotted lines) to which is bound non-fluorescent WGA.

Those skilled in the art would readily appreciate that all parameters and configurations described herein are meant to be exemplary and that actual parameters and configurations will depend upon the specific application for which the systems and methods of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described. The present invention is directed to each individual feature, system, or method described herein. In addition, any combination of two or more such features, systems or methods, provided that such features, systems, or methods are not mutually inconsistent, is included within the scope of the present invention.

What is claimed:

1. A method comprising:
    establishing a flowing stream of a fluid against a surface of a cell, the stream including at least first and second components in contact with first and second portions of the cell, respectively, the first component including therein at a first concentration a substance able to bind to the surface of the cell, permeate across the cell plasma membrane into the interior of the cell, or both, the second component of the stream having a second concentration of the substance therein; and
    binding the substance to the surface of the first portion of the cell, permeating the substance across the cell plasma membrane of the first portion of the cell, or both, to an extent different than that at the second portion of the cell.

2. The method as in claim 1, wherein the first concentration of the substance is essentially uniform in at least a portion of the first component of the flowing stream.

3. The method as in claim 2, wherein both the first and second concentrations are essentially uniform in at least a portion of the first component of the flowing stream and at least a portion of the second portion of the flowing stream, respectively.

4. The method as in claim 1, wherein the cell is attached to a surface of a substrate during the establishing and binding steps.

5. The method as in claim 1, wherein at least one of the first and second portions of the cell contacted by the flowing stream comprises a main body portion of the cell.

6. The method as in claim 1, wherein the flowing stream is characterized by laminar flow.

7. The method as in claim 6, wherein the establishing step comprises the steps of:
    establishing a flowing stream of a fluid comprising the first component in a first channel;
    separately establishing a flowing stream of a fluid comprising the second component in a second channel; and
    converging the flowing stream of the fluid comprising the first component and the flowing stream of the fluid comprising the second component together so that they flow parallel, adjacent to, and in contact with each other in a third channel, thereby forming a composite flowing stream comprising the first and second component.

8. The method as in claim 1, further comprising the step of:
    establishing within the cell a gradient of an active substance.

9. The method as in claim 8, wherein the first component of the flowing stream supplies the substance able to bind to the surface of the cell, permeate across the cell plasma membrane into the interior of the cell, or both to the first portion, and the second component of the flowing stream removes the substance able to bind to the surface of the cell, permeate across the cell plasma membrane into the interior of the cell, or both from the second portion of the cell.

10. The method as in claim 9, wherein the second component of the stream is essentially free of the substance able to bind to the surface of the cell, permeate across the cell plasma membrane into the interior of the cell, or both.

11. The method as in claim 9, wherein the gradient of the active substance established within the cell is characterized by the existence of a first region within the cell, proximate to at least a portion of the first portion of the exterior of the cell, having a first concentration of the active substance and the existence of a second region within the cell, proximate to at least a portion of the second portion of the exterior of the cell, having a second concentration of the active substance, the first concentration of the active substance differing from the second concentration of the active substance by at least about 5% at a time exceeding about 5 min after the commencement of the establishment of a gradient within the cell.

12. The method as in claim 11, wherein the gradient established within the cell is essentially a steady state gradient.

13. The method as in claim 9, wherein the gradient established within the cell is a gradient of active substance that is freely diffusable within the cell.

14. The method as in claim 9, wherein the substance able to bind to the surface of the cell, permeates across the cell plasma membrane into the interior of the cell, or both and the active substance are the same substance.

15. The method as in claim 11, further comprising the step of:
    detecting, for each of the first and second regions, at least one parameter indicative of a spatial distribution of the concentration of the active substance within the cell.

16. The method as in claim 15, further comprising the step of:
determining from the at least one measured parameter a measure of the relative permeability of a plasma membrane of the cell to the active substance.

17. The method as in claim 15, further comprising the step of:
determining from the at least one measured parameter a measure of the relative thickness of the cell at a selected location.

18. The method as in claim 14, wherein the active substance passively permeates across the cell plasma membrane.

19. The method as in claim 14, wherein the active substance permeates across the cell plasma membrane via an active transport process.

20. The method as in claim 14, wherein the active substance is a substance able to disrupt or stabilize a cytoskeleton of the cell.

21. The method as in claim 14, wherein the active substance is a substance able to localize in a subcellular organelle of the cell.

22. The method as in claim 21, wherein the subcellular organelle is mitochondria.

23. The method as in claim 14, wherein the active substance is an anti-cancer drug.

24. The method as in claim 8, wherein the active substance comprises calcium ions.

25. The method as in claim 1, wherein the substance binds to a selected type of receptor on the surface of the cell during the binding step.

26. The method as in claim 25, wherein, subsequent to binding to the selected type of receptor, the substance is endocytosed into the interior of the cell.

27. The method as in claim 25, wherein, binding of the substance to the selected type of receptor acts as a signal to cause a biochemical or biophysical effect within the cell.

28. The method as in claim 1, wherein the flowing stream established during the establishing step includes first, second, and third components in contact with first, second, and third portions of the cell respectively.

29. The method as in claim 1, wherein the first and second components of the flowing stream are adjacent to each other defining a boundary therebetween, further comprising the step of:
carrying out a biophysical or biochemical interaction at a portion of the cell proximate the boundary selectively, to an extent different than that at portions of the cell not proximate the boundary.

30. A method comprising:
selectively providing to a first portion of the exterior of a cell a first flowing fluid containing a substance able to effect a biochemical or biophysical interaction within the cell;
selectively providing to a second portion of the exterior of the cell a second flowing fluid removing from the second portion of the exterior of the cell said substance; and thereby
establishing within the cell a gradient of an active substance.

31. The method as in claim 30, wherein during the establishing step the gradient of the active substance is characterized by the existence of a first region within the cell, proximate to at least a portion of the first portion of the exterior of the cell, having a first concentration of the active substance and the existence of a second region within the cell, proximate to at least a portion of the second portion of the exterior of the cell, having a second concentration of the active substance, the first concentration of the active substance differing from the second concentration of the active substance by at least about 5% at a time exceeding about 5 min after the commencement of the providing steps.

32. The method as in claim 31, wherein the gradient established within the cell is essentially a steady state gradient.

33. The method as in claim 30, wherein the gradient established within the cell is a gradient of active substance that is freely diffusable within the cell.

34. The method as in claim 30, wherein the substance able to effect a biochemical or biophysical interaction within the cell contained in the first flowing fluid and the active substance are the same.

35. The method as in claim 30, wherein the concentration of the substance able to effect a biochemical or biophysical interaction within the cell is essentially uniform in a least a portion of the first flowing fluid and the concentration of the substance able to effect a biochemical or biophysical interaction within the cell is essentially uniform in a least a portion of the second flowing fluid.

36. A method comprising:
selectively exposing a first portion of the exterior of a cell to a first fluid containing a substance able to effect a biochemical or biophysical interaction within the cell, the first portion of the exterior of the cell comprising a portion of a main body of the cell; and
selectively exposing a second portion of the exterior of the cell to a second fluid removing from the second portion of the exterior of the cell said substance; and thereby
establishing within the cell a gradient of an active substance, characterized by the existence of a first region within the cell, proximate to at least a portion of the first portion of the exterior of the cell, having a first concentration of the active substance and the existence of a second region within the cell, proximate to at least a portion of the second portion of the exterior of the cell, having a second concentration of the active substance, the first concentration of the active substance differing from the second concentration of the active substance by at least about 5% at a time exceeding about 5 min after the commencement of the exposing steps.

37. The method of claim 36, wherein at least one of the first and second fluids is flowing.

38. The method of claim 37, wherein both of the first and second fluids are flowing.

39. The method of claim 36, wherein the gradient established within the cell is an essentially steady state gradient.

40. The method of claim 36, wherein the substance contained in the first fluid is able to permeate across a plasma membrane of the cell.

41. The method of claim 40, wherein the substance contained in the first fluid and the active substance are the same.

42. The method of claim 36, wherein the gradient established within the cell is a gradient of active substance that is freely diffusable within the cell.

43. A method comprising:
establishing within a cell a gradient of a freely diffusable active substance, characterized by the existence of a first region within the cell having a first concentration of the active substance and the existence of a second region within the cell having a second concentration of the active substance, the first concentration of the active substance differing from the second concentration of the active substance by at least about 5% at a time exceeding about 5 min after the commencement of the establishment of the gradient.

44. A method comprising:

creating a first region within a cell of a selected cell type, the first region containing freely diffusable active substance, the first region comprising a portion of a main body of the cell;

creating a second region within the cell essentially free of freely diffusable active substance; and detecting, for each of the first and second regions, at least one parameter indicative of a response of the cell to the active substance determinative of the efficacy of a treatment with the active substance on the cell type.

45. The method of claim 44, wherein the creating steps comprise the steps of:

selectively exposing a first portion of the exterior of the cell, at least a portion of which is proximate the first region within the cell, to a first fluid containing a substance able to effect a biochemical or biophysical interaction within the cell; and selectively exposing a second portion of the exterior of the cell, at least a portion of which is proximate to the second region within the cell, to a second fluid removing from the second portion of the exterior of the cell said substance able to effect a biochemical or biophysical interaction within the cell.

46. The method of claim 45, wherein the first and second fluids are flowing.

47. A method comprising:

allowing a substance to bind to a first region of the exterior of a cell membrane of a selected cell type;

creating a second region of the exterior of the cell membrane that is essentially free of the bound substance; and detecting, for each of the first and second regions, at least one parameter indicative of a response of the cell to the bound substance determinative of the efficacy of a treatment with the substance on the cell type.

48. The method as in claim 47, wherein the allowing and creating steps comprise the steps of:

selectively exposing the first region of the exterior of the cell to a first fluid containing the substance; and selectively exposing the second region of the exterior of the cell to a second fluid not containing the substance.

49. The method as in claim 48, wherein the first and second fluids are flowing.

50. An article comprising:

a substrate having at least one cell positioned on a surface of the substrate; and a flowing fluid stream in contact with the surface, the stream including at least first and second components in contact with first and second portions of the cell, respectively, the first component including therein at a first, essentially uniform concentration a substance able to bind to an exterior surface of the cell, permeate across the cell membrane into the interior of the cell, or both, the second component of the stream having a second, essentially uniform concentration of the substance therein.

51. The article as in claim 50, further comprising:

a microfluidic network including at least one microfluidic flow channel constructed and arranged to contain the flowing fluid stream.

52. The article as in claim 51, wherein the microfluidic network is at least partially comprised of an elastomer.

53. The article as in claim 52, wherein the elastomer comprises poly(dimethylsiloxane).

54. A method comprising:

selectively providing to a first portion of the plasma membrane of a cell a first flowing fluid containing therein a substance, which is able to permeate across the plasma membrane, at a concentration exceeding or equal to a maximum concentration of the substance within the cell; and selectively providing to a second portion of the plasma membrane of the cell a second flowing fluid containing therein a concentration of the substance, which is able to permeate across the plasma membrane, less than or equal to a minimum concentration of the substance within the cell.

55. A method comprising:

establishing a flowing stream of a fluid against a surface of a cell, the stream including at least first, second and third components in contact with first, second, and third portions of the cell, respectively, the second component of the stream being interposed between the first component of the stream and the third component of the stream, the first component of the stream and the third component of the stream each carrying a different potential for a biophysical or biochemical interaction with the cell than the second component of the stream; and carrying out the biophysical or biochemical interaction at the first and third portions of the cell to an extent different than at the second portion of the cell.

56. The method as in claim 55, wherein the first component of the stream carries a different potential for a biophysical or biochemical interaction than the third component of the stream.

57. The method as in claim 55, wherein each of the first, second, and third components of the flowing stream includes at least a portion thereof wherein the potential for a biophysical or biochemical interaction with the cell is essentially uniform throughout that portion.

58. The method as in claim 55, wherein the potential for a biophysical or biochemical interaction with the cell of a component of the flowing stream is proportional to the concentration of a substance within the component.

59. The method as in claim 58, wherein the substance chemically reacts with the surface of the cell.

60. The method as in claim 59, wherein the substance degrades a molecule attached to the surface of the cell.

61. The method as in claim 59, wherein the substance is able to bind to the surface of the cell.

62. The method as in claim 59, wherein the substance is able to permeate across a plasma membrane of the cell into the interior of the cell.

63. The method as in claim 58, wherein the substance within the first component is different from the substance within the second component and the substance within the third component, and the substance within the second component is different than the substance within the third component.

64. The method as in claim 55 further comprising the step of;

detecting, for each of the first, second, and third portions of the cell at least one parameter indicative of a response of the cell to the biophysical or biochemical interaction at the first, second, and third portions of the cell.

65. A method comprising:

establishing a flowing stream of a fluid, the stream including at least first and second components adjacent to each other and defining therebetween a boundary; and carrying out a biophysical or biochemical interaction at a first portion of a cell proximate the boundary selectively, to an extent different than at a second portion of the cell.

66. The method as in claim 65, wherein the first and second components include first and second reactants respectively.

67. The method as in claim 66, further comprising the steps of:

allowing a chemical reaction to occur at the boundary, the chemical reaction producing a product able to effect a biochemical or biophysical interaction within the cell.

68. The method as in claim 67, wherein the product produced by the chemical reaction comprises nitric oxide.

* * * * *